United States Patent [19]

Boden et al.

[11] 4,342,663
[45] Aug. 3, 1982

[54] USE OF MIXTURE OF ALIPHATIC $C_{10}$ BRANCHED OLEFINS IN AUGMENTING OR ENHANCING THE AROMA OF ARTICLES SUBJECTED TO ACTION OF AQUEOUS HYPOCHLORITES

[75] Inventors: Richard M. Boden, Monmouth Beach; Lambert Dekker, Wykoff; Frederick L. Schmitt, Holmdel, all of N.J.; Augustinus G. Van Loveren, Rye, N.Y.

[73] Assignee: International Flavors & Fragrances, Inc., New York, N.Y.

[21] Appl. No.: 231,771

[22] Filed: Feb. 5, 1981

Related U.S. Application Data

[63] Continuation-in-part of Ser. No. 188,576, Sep. 18, 1980, Pat. No. 4,303,555, which is a continuation-in-part of Ser. No. 160,788, Jun. 19, 1980, Pat. No. 4,287,084.

[51] Int. Cl.³ .................. C11D 7/54; C11D 3/395; C11D 3/50
[52] U.S. Cl. .................. 252/186.36; 252/95; 252/99; 252/174.11; 252/522 R; 8/108 R; 8/108 A; 252/316; 252/187.25; 252/187.26
[58] Field of Search .......... 252/95, 187 H, 99, 174.11, 252/522 R; 8/108 R, 108 A

[56] References Cited

U.S. PATENT DOCUMENTS

| | | | |
|---|---|---|---|
| 3,684,722 | 8/1972 | Hynams et al. | 252/187 H |
| 4,113,645 | 9/1978 | DeSimmons | 252/187 H |
| 4,123,377 | 1/1978 | Davey et al. | 252/187 H |
| 4,208,297 | 6/1980 | Light et al. | 252/522 R |

*Primary Examiner*—Irwin Gluck
*Attorney, Agent, or Firm*—Arthur L. Lieberman

[57] ABSTRACT

Described are methods for augmenting or enhancing the aroma of articles subjected to the action of aqueous hypochlorite bleach compositions by adding perfume aroma augmenting or enhancing quantities of aliphatic $C_{10}$-branched olefin-containing mixtures produced by dimerizing isoamylene, (2-methyl-2-butene) to aqueous alkali metal hypochlorite bleach compositions containing a stabilizindg and emulsifying quantity of at least one compound having the structue:

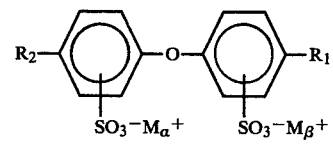

wherein at least one of $R_1$ and $R_2$ represents $C_{10}$–$C_{12}$ branched or straight chain alkyl an when one of $R_1$ or $R_2$ is $C_{10}$–$C_{12}$ branched or straight chain alkyl, the other of $R_1$ or $R_2$ is hydrogen and wherein $M_\alpha$ and $M_\beta$ are the same or different and each represents alkali metal which may be either sodium, potassium or lithium and aqueous bleaching compositions containing such dimerized isoamylene, aqueous metal hypochlorite and at least one compound having the structure:

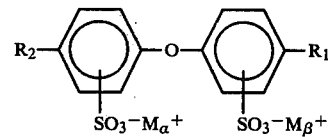

wherein $R_1$, $R_2$, $M_\alpha$ and $M_\alpha$ are defined as above.

5 Claims, 14 Drawing Figures

GLC PROFILE FOR EXAMPLE I.

GLC PROFILE FOR EXAMPLE I.

GLC PROFILE FOR EXAMPLE I.

GLC PROFILE FOR EXAMPLE I.
DISTILLATION PRODUCT.

GLC PROFILE FOR EXAMPLE I.
CRUDE PRODUCT.

NMR SPECTRUM FOR PEAK I OF EXAMPLE I, OF GLC OF FIG. IE

IR SPECTRUM FOR EXAMPLE I, PEAK I, OF GLC OF FIG. IE.

NMR SPECTRUM FOR EXAMPLE I, PEAK 2, OF GLC OF FIG. 1E

IR SPECTRUM FOR EXAMPLE I, PEAK 2 OF GLC OF FIG. 1E

NMR SPECTRUM FOR PEAK 2 OF EXAMPLE I, OF GLC OF FIG. IB.

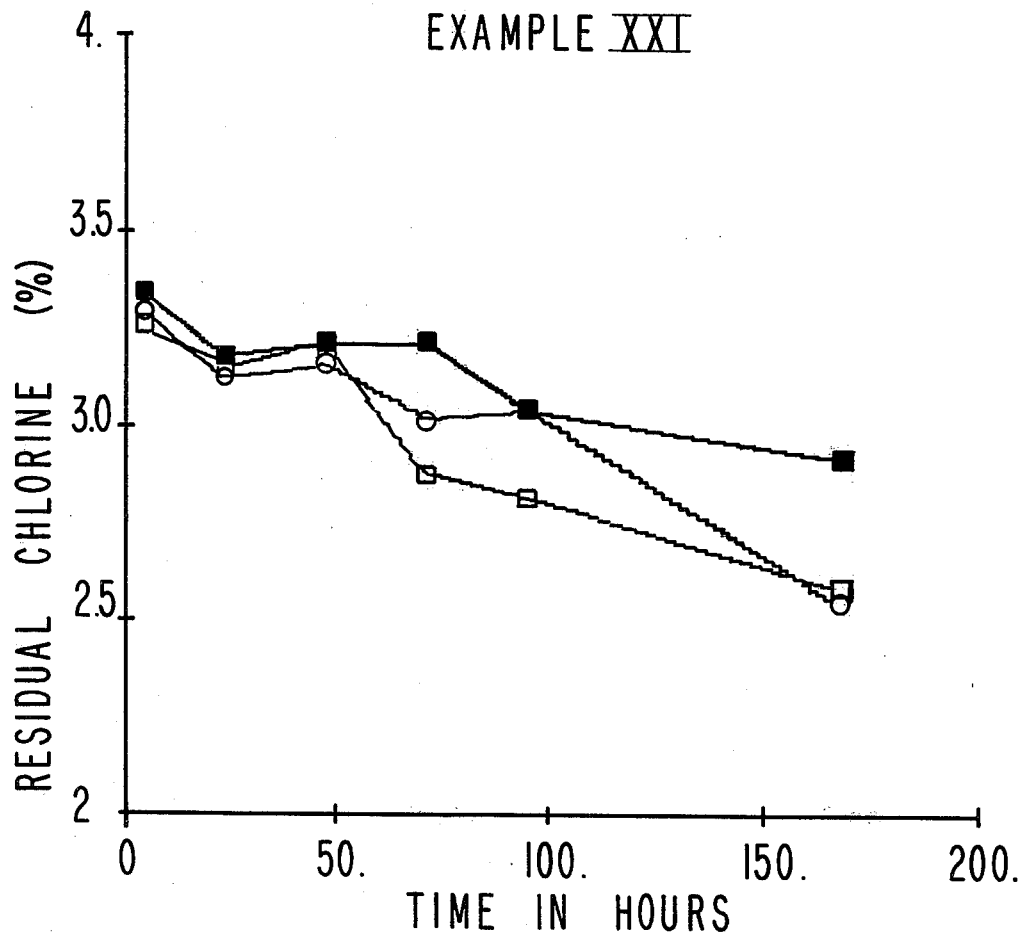

EXAMPLE XXI

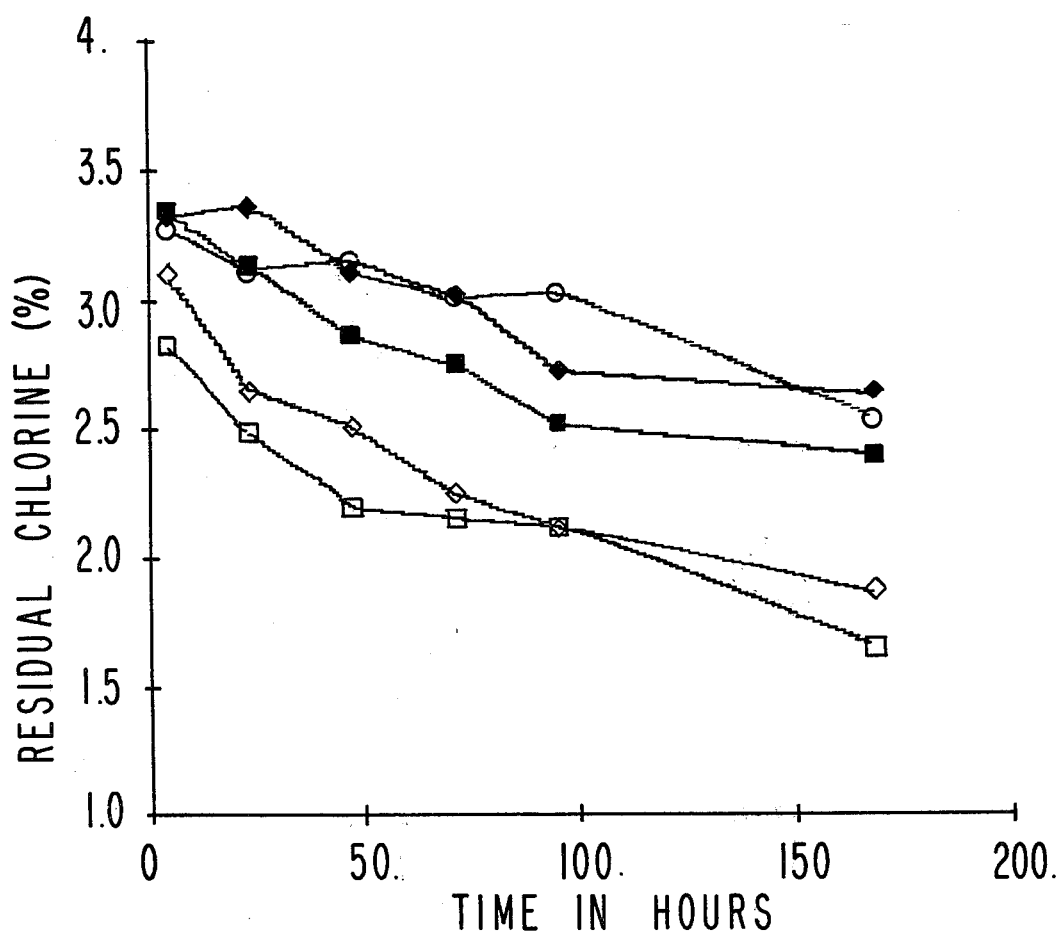

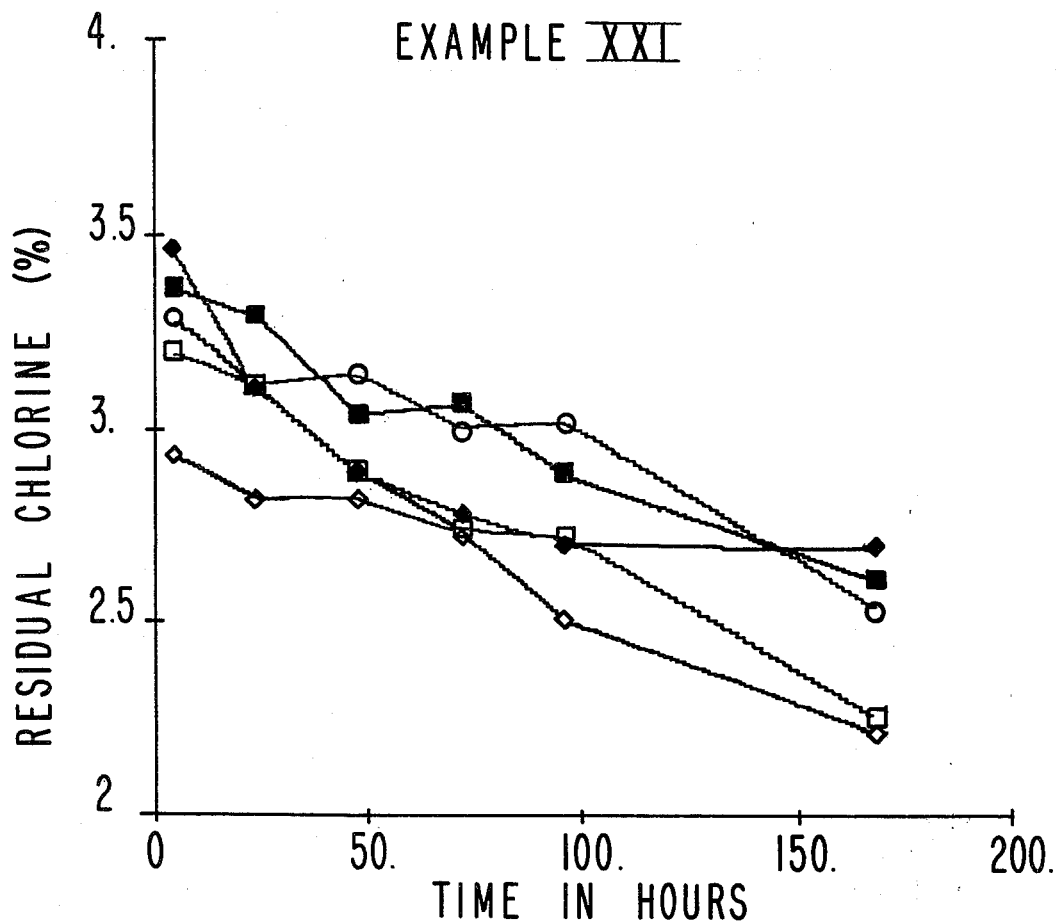

USE OF MIXTURE OF ALIPHATIC $C_{10}$ BRANCHED OLEFINS IN AUGMENTING OR ENHANCING THE AROMA OF ARTICLES SUBJECTED TO ACTION OF AQUEOUS HYPOCHLORITES

This application is a continuation-in-part of application for U.S. patent, Ser. No. 188,576, filed on Sept. 18, 1980, now U.S. Pat. No. 4,303,555, which, in turn, is a continuation-in-part of application for U.S. patent, Ser. No. 160,788, filed on June 19, 1980, now U.S. Pat. No. 4,287,084.

BACKGROUND OF THE INVENTION

The instant invention provides mixtures of $C_{10}$ branched chain olefins which are used to augment or enhance the aroma of articles (e.g. clothing) subjected to the bleaching action of aqueous hypochlorite solutions subsequent to the drying of said articles after being subjected to such bleaching action. The instant invention also covers hypochlorite compositions which comprise aqueous hypochlorite, the said $C_{10}$ branched chain olefins and one or more compounds having the generic structure:

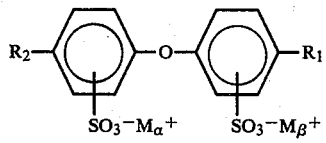

wherein at least one of $R_1$ and $R_2$ represents $C_{10}$-$C_{12}$ branched or straight chain alkyl and when one of $R_1$ or $R_2$ is $C_{10}$-$C_{12}$ branched or straight chain alkyl, the other of $R_1$ or $R_2$ is hydrogen; and when $M_\alpha$ and $M_\beta$ are the same or different and each represents sodium, potassium or lithium, said $C_{10}$-$C_{12}$ moieties being either straight chain or branched chain, for example, having the structures:

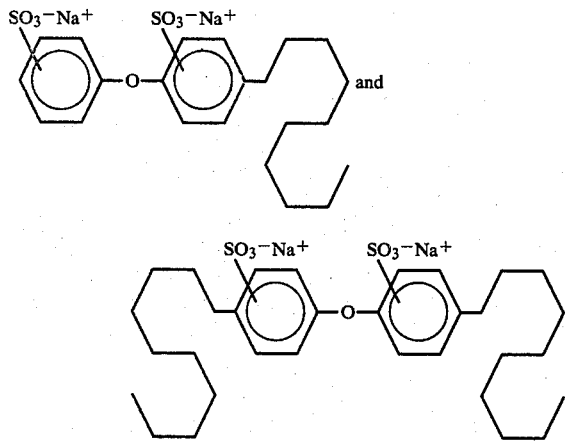

wherein the $SO_3^-Na^+$ groups are at various positions on the phenyl moieties.

Chemical compounds which can provide woody, piney and herbaceous aromas are desirable in the art of perfumery as well as in hypochlorite bleaches which include such perfuming materials. Many of the natural materials which provide such fragrances and contribute such desired nuances to perfumery compositions are high in cost, unobtainable at times, vary in quality from one batch to another, are unstable in aqueous hypochlorite bleaches, and/or are generally subject to the usual variations of natural products.

There is, accordingly, a continuing effort to find synthetic materials which will replace, enhance or augment the fragrance notes provided by certain natural essential oils or compositions thereof, particularly where perfumery materials which are stable in hypochlorite bleach compositions are desired. Unfortunately, many of the synthetic materials either have the desired nuances only to a relatively small degree, or they contribute undesirable or unwanted odor to the compositions and their stability, in most instances, is relatively low in the presence of aqueous hypochlorite bleaching solutions.

Aliphatic hydrocarbons are well known in the art of perfumery, e.g. myrcene, 2-methyl-6-methylene-2,7-octadiene, a constituent of lemon grass oil. Also found in lemon oil as well as in Bergamot oil, according to Gildemeister and Hoffmann, (Die Atherischen Ole, 3rd edition, Volume 1, page 301) is octylene, a long chain olefin containing eight carbon atoms.

Arctander, "Perfume and Flavor Chemicals, (Aroma Chemicals)", 1969, Vol. I, at monograph 974, discloses the use of "di-isoprene" in perfumery. Arctander states that di-isoprene is a mixture of 2,6-dimethyl-2,6-octadiene; 2,7-dimethyl-2,6-octadiene; and 3,6-dimethyl-2,6-octadiene. Arctander states that this material has a sweet, diffusive, somewhat "gassy" odor and, overall, is of very "little interest to the perfumer." At monograph 1074, Arctander discloses "dipentene" having a use in perfumery and indicates that this "dipentene" is 1-methyl-4-iso-propenyl-1-cyclohexane and indicates that it is useful in perfumery as a "lift" in citrusy fragrances and in the reconstruction of many essential oils such as Bergamot, Lime and Lemon.

Nothing in the prior art discloses the use in conjunction with aqueous hypochlorite bleaching agents and with compounds having the generic structure:

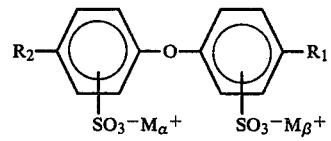

wherein one or both of $R_1$ or $R_2$ is branched or straight chain $C_{10}$-$C_{12}$ alkyl and if one of $R_1$ or $R_2$ is $C_{10}$-$C_{12}$ straight or branched chain alkyl, the other of $R_1$ or $R_2$ is hydrogen and wherein $M_\alpha$ and $M_\beta$ are the same or different and each is sodium, lithium or potassium, of diisoamylenes defined according to the generic structure:

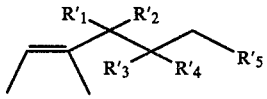

wherein $R_1'$, $R_2'$, $R_3'$, $R_4'$ and $R_5'$ are the same or different and each represents hydrogen or methyl with the proviso that (i) the sum total of the carbon atoms in $R_1'$, $R_2'$, $R_3'$, $R_4'$ and $R_5'$ is 3; and (ii) $R_1'$ and $R_2'$ represents hydrogen where $R_5'$ represents methyl; and (iii) when either $R_1'$ or $R_2'$ is methyl, $R_5'$ is hydrogen.

Furthermore, considerable difficulties have heretofore been encountered in using such compounded hypochlorite bleach or sterilizing solutions with perfumed oils so that a stable long-lasting single phase commercially feasible bleach or sterilizing solution has been difficult to obtain, particularly wherein the desired aroma of the article bleached or sterilized (e.g. clothing) has a woody, piney and/or herbaceous faint aroma on drying (and not the usual "hypochlorite-bleached-article" aroma). The problem has been defined in United Kingdom Patent Specification No. 886,084, published on Jan. 3, 1962 wherein it is stated that a stable "dispersion" of hypochlorite-resistant perfume in aqueous solutions of hypochlorites was formulated. United Kingdom Patent Specification No. 886,084 discloses the preparation of an aqueous "solution" of a hypochlorite containing a hypochlorite resistant perfume and a surface active quaternary ammonium compound of the betaine type soluble in the hypochlorite solution. Such ammonium compounds have the generic structure:

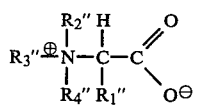

wherein each of $R_1''$, $R_2''$, $R_3''$ and $R_4''$ are alkyl. One of the features of the perfumed solutions produced in accordance with said United Kingdom Patent Specification No. 886,084 is indicated to be that the solution exhibits foaming properties. Another feature of United Kingdom Patent Specification No. 886,084 is stated to be that the perfumed solutions covered by the patent are found to be clear and homogeneous after eight weeks of storage at room temperature. Nevertheless, betaines such as "Ambiteric D" as are discussed therein are not so broadly useful when used in concentrations of from 0.15% up to 4.0% (based on total weight of bleach or sterilizing solution) as to have the ability to be used in conjunction with woody, piney or herbaceous types of perfume oils which should be incorporated into hypochlorite bleaches or sterilizers so that long lasting stable soluble single phase perfumed aqueous alkali metal hypochlorite bleach or sterilizing solutions having woody or piney or herbaceous long lasting stable aromas are obtained, particularly where the quantity of perfume oil in the bleach or sterilizing substance is at levels of between 0.02% and 0.8% by weight of the total bleach or sterilizing solution. The need for the "woody", "piney" or "herbaceous" aromas to be present in such bleach or sterilizing solutions exists so that the disagreeable characteristic "hypochlorite" aroma is substantially eliminated from aromas of the product to which the bleach or sterilizing solution is applied; particularly on dry-out, as well as from the aroma of the hands of the user when they are in direct contact with such bleach or sterilizing solutions.

U.S. Pat. No. 3,560,389 also discloses the feasibility of using perfume oils in hypochlorite bleaches or sterilizers at column 3, lines 37–40 but the disclosure is limited to inclusion of various detergents in addition to amine oxides, such as lithium lauryl sulfate and sodium lauryl ether sulfate and/or is further limited to include hydrotropes such as sodium xylene sulfonate in addition to the amine oxide. Exclusion of such hydrotropes and detergents additional to the amine oxides and diphenyl oxide derivatives of our invention is desirable not only to cause the perfume oils (which have the desired "piney" or "woody" or "herbaceous" aromas) to function properly, but also from an ecological standpoint.

European Chemical News, Volume 13, Jan. 18, 1968, sets forth a synopsis of South African Pat. No. 67/4667 which corresponds to U.S. Pat. No. 3,560,389, but the reference also states at page 42:

"Alternatively, a detergent with bleaching or bactericidal properties can be formulated. Perfuming bleaching solutions is now possible."

Neither the South African nor the U.S. patents, however, indicate the advantages and usefulness of limiting the detergents either to (a) compounds having the generic structure:

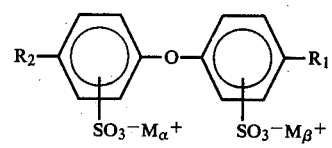

wherein at least one of $R_1$ and $R_2$ represents $C_{10}$–$C_{12}$ straight chain or branched chain alkyl and when one of $R_1$ or $R_2$ is $C_{10}$–$C_{12}$ branched or straight chain alkyl, the other or $R_1$ or $R_2$ is hydrogen and wherein $M_\alpha$ and $M_\beta$ are the same or different and each represents alkali metal which may be sodium, lithium or potassium, or (b) to mixtures of compounds having the structure:

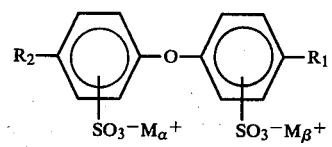

with one or more amine oxides having the structure:

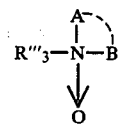

of excluding from the formulation a hydrotrope or of specifying the nature of the perfume oil useful in the perfumed bleach or sterilizing solution (wherein A and B are each separately methyl or taken together, complete a morpholino ring and wherein $R_3'''$ is straight chain alkyl having from 11 up to 13 carbon atoms).

U.S. Pat. No. 3,876,551 in attempting to solve the foregoing problem discloses a stable single phase aqueous alkali metal hypochlorite liquid perfume bleach or sterilizing composition comprising an aqueous mixture of (1) an amine oxide composition consisting essentially of at least one morpholino- and/or dimethyl ($C_{11}$–$C_{13}$ straight chain alkyl) amine oxide in an amount greater than 55% of said amine oxide composition, (2) at least one alkali metal hydroxide, (3) at least one alkali metal hypochlorite, and (4) a perfume oil compatible with the mixture capable of imparting a "woody" or a "floral" or a "clean fresh" or a "musk" or a "citrusy" note to the bleach or sterilizing composition; the mixture having a pH in the range of from 12 to 13.5 and the mixture excluding hydrotropes as well as all surfactants except the amine oxide. U.S. Pat. No. 3,876,551 also attempts to solve the foregoing problem by disclosing a process for producing the above-name mixture comprising the steps of combining an amide oxide composition consisting essentially of one or more morpholino and/or dimethyl $C_{11}$–$C_{13}$ straight chain alkyl amine oxide(s) with the perfumed oil to form an amine oxide-perfume oil premix; admixing the amine oxide-perfume oil premix with an aqueous alkali metal hypochlorite solution, and combining an alkali metal hydroxide with the solution whereby the final pH of the mixture is from 12 up to 13.5. In a further effort to solve the foregoing problem U.S. Pat. No. 3,876,551 also discloses adjustment of the pH of the aqueous metal hypochlorite solution initially to the range of 12–13.5 and the combining the resulting pH-adjusted aqueous hypochlorite solution with the aforementioned premix. The resulting composition is indicated to cause products to which said composition is applied to have eliminated therefrom the disagreeble characteristic "hypochlorite" aroma and instead to have a "clean fresh" or "floral" or "woody" or "musk" or "citrusy" aroma to be imparted to the treated products. In addition, it is stated that the hands of the individual user after using and being in direct contact with the hypochlorite composition will not have the disagreeable characteristic "hypochlorite" aroma but instead will have a pleasant "clean fresh" or "floral" or "woody" or "musk" or "citrusy" aroma.

The disadvantage of the system of U.S. Pat. No. 3,876,551 however, concerns the relatively low degree of chemical stability and substantive stability of the perfume oil and of the single liquid phase system. Nothing in U.S. Pat. No. 3,876,551 indicates such a high degree of stability of the perfume-hypochlorite system as exists in the liquid or gel system of the present invention. Indeed, the stabilities using the system of the instant invention are far greater even at levels as low as 3% hypochlorite and is also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the systems taught in the prior art.

Furthermore, nothing in the prior art including the teaching of U.S. Pat. No. 3,876,551 states either explicitly or implicitly the compatability of a thickener in the instant system, such as sodium palmitate, sodium stearate, potassium palmitate potassium stearate, sodium laurate or lithium laurate or lithium stearate or lithium palmitate whereby a stable gel (as opposed to a liquid) phase perfumed hypochlorite system may be produced.

The combination of the compound group having the structure:

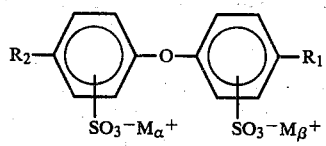

(wherein $R_1$, $R_2$, $M_\alpha$ and $M_\beta$ are defined, supra) with perfume and hypochlorite bleach in general, is set forth in the Kao Soap Company, Japanese Pat. No. 25514/79 filed on Nov. 2, 1973 and opened for public inspection on June 19, 1975. Thus, on page 2, at column 4, line 15, the compound:

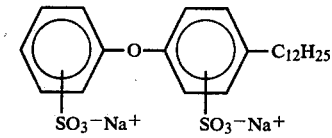

is disclosed for use in conjunction with the perfumed hypochlorite bleaches. The claim of the Kao Soap Patent is as follows:

CLAIM: An aromatic liquid bleaching composition containing, as active ingredient, sodium hypochlorite, which comprises one or more of simple perfumes or compounded perfumes selected from the group consisting of anisole, benzophenone, benzylphenyl ether, bromelia, cedrenyl acetate, p-tertiary butylcyclohexanol, dimethylbenzylcarbinyl acetate, dihydroterpinyl acetate, diphenyl oxide, dimethylbenzylcarbinol, dimethylphenylcarbinol, dihydroterpineol, fenchyl acetate, fenchyl alcohol, p-methyldimethylbenzylcarbinol, methylphenylcarbinyl acetate, methyl-n-valerate, muskmoskene, muscarone, methylamyl ketone, phenylethyldimethylcarbinyl acetate, rose phenone, styrallyl propionate, tetra hydromuguol, tetra hydromuguyl acetate, tetrahydrolinalool, tetrahydrolinalyl acetate, verool, velveton, verdox, coniferan and yarayara, and a surface active agent which can stably be dissolved in an aqueous solution of sodium hypochlorite.

Furthermore, the use of such compounds as those having the structure:

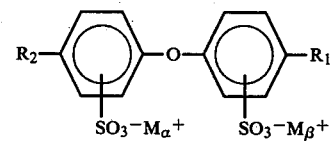

(wherein $R_1$, $R_2$, $M_\alpha$ and $M_\beta$ have been previously defined) with hypochlorite bleaches is documented in the brochure of Dow Chemical entitled "DOWFAX Surfactants" and is covered in the Dow Chemical Company Pat. No. 3,172,861 issued on Mar. 9, 1965.

Nothing in the prior art discloses, however, the utility of the diisoamylene mixture or individual compounds of the instant application taken together with one of the compounds defined according to the generic structure:

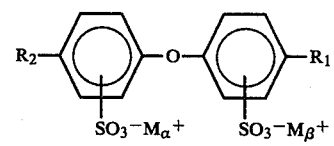

(wherein $R_1$, $R_2$, $M_\alpha$ and $M_\beta$ have been defined, supra) in hypochlorite bleaches, particularly where the hypochlorite concentration is greater than 7%. More particularly, nothing in the prior art discloses the use of such systems in conjunction with a thickener such as sodium palmitate, potassium palmitate, sodium stearate, potassium stearate, sodium laurate, potassium laurate lithium laurate, lithium stearate or lithium palmitate, whereby a stable gelled perfumed hypochlorite is formed.

"Di-isoamylene" is indicated to be synthesized in the following references:

i—Murphy & Lane, Ind. Eng. Chem., Prod. Res. Dev., Vol. 14, No. 3, 1975 p.167 (Title: Oligomerization of 2-Methyl-2-Butene in Sulfuric Acid and Sulfuric-Phosphoric Acid Mixtures).

ii—Whitmore & Mosher, Vol. 68, J. Am. Chem. Soc. February, 1946, p. 281 (Title: The Depolymerization of 3,4,5,5-Tetramethyl-2-hexene and 3,5,5-Trimethyl-2-heptene in Relation of the Dimerization of Isoamylenes)

iii—Whitmore & Stahly, Vo. 67, J. Am. Chem. Soc., December, 1945, p. 2158 (Title: The Polymerization of Olefins. VIII The Depolymerization of Olefins in Relation of Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2 p. 796 (Production of Di-isoamylene From Isoamylene Using Mercury Acetate Catalyst)

United Kingdom Pat. No. 796,130 published on June 4, 1958 discloses the synthesis of polyalkylindanes by means of, interalia, reacting alpha-methylstyrene with trimethylethene (2-methylbutene-2) in the presence of an acid catalyst such as sulfuric acid or boron trifluoride diethyletherate. It is further indicated that such compounds are useful intermediates in the production of perfumery compounds. Apparently, however, the more volatile di-isoamylenes produced as side-products in the reaction of 2-methyl-butene-2 with alpha-methylstyrene are discarded.

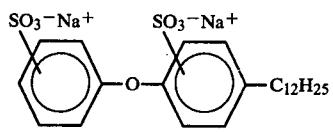

wherein the $SO_3^-Na^+$ moieties are at various positions on the phenyl moieties and the $C_{12}H_{25}$ moiety represents various branched chain alkyl moieties having 12 carbon atoms each, or (ii) AROMOX ® DMMC-W, a 30% aqueous solution of dimethylcocoamine oxide having the structure:

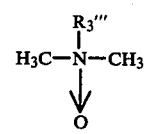

a trademark of the Akzo Corporation of Chicago, Ill. (product produced by Armac, Division of Akzo Corporation of Chicago, Ill.) with the weight ratio of AROMOX ® DMMC-W:base being 0.8:99 and the ratio of DOWFAX ® 2A:base being 0.8:99, as described in Example XXI, infra.

Figure 5B:
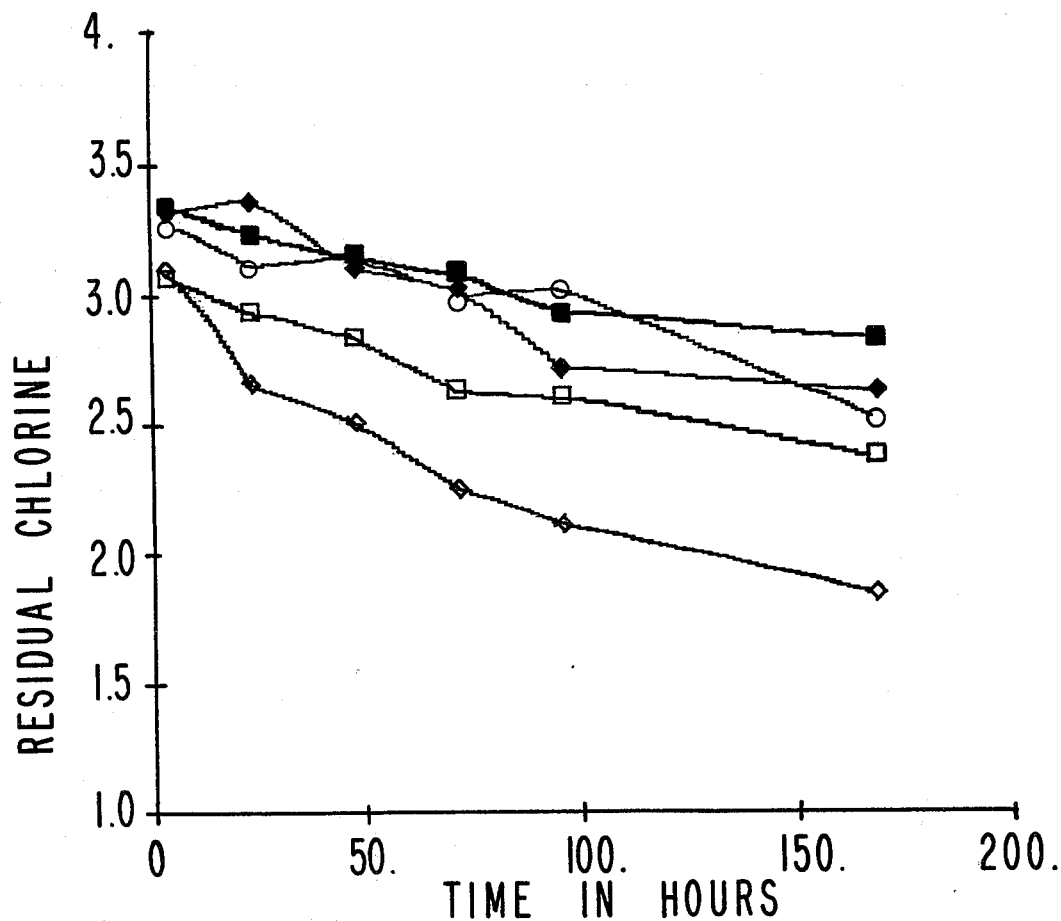
FIG. 5A represents a graph of percent residual chlorine versus time in hours for hypochlorite solutions containing either (i) DOWFAX ® 2A1 (a registered trademark of the Dow Chemical Company of Midland, Mich.) identifying a mixture of compounds defined according to the structure.

FIG. 5B is a graph of percent residual chlorine versus time in hours for hypochlorite solutions of either (i) DOWFAX ® 2A1 or (ii) AROMOX ® DMMC-W, in the absence of fragrance or essential oils with the weight ratio of AROMOX ® DMMC-W:base being 1.8:99 and 3.8:96 and the ratios of DOWFAX ® 2A1:base being 1.8:99 and 3.8:99, as described in Example XXI, infra.

FIG. 6A is a graph of percent residual chlorine versus time in hours comparing the performance of hypochlorite solutions of (i) DOWFAX ® 2A1 versus (ii) AROMOX ® DMMC-W using one of the diisoamylene products produced according to Example I, infra, or not using any fragrance or essential oils, with the weight ratio of AROMOX ® DMMC-W:diisoamylene:base being 3.8:0.2:96 and the ratio of DOWFAX ® 2A1:diisoamylene:base being 3.8:0.2:96, as described in Example XXI, infra.

FIG. 6B is a graph of percent residual chlorine versus time in hours comparing hypochlorite solutions of (i) DOWFAX ® 2A1 versus (ii) AROMOX ® DMMC-W, with the perfuming material being one of the diisoamylene products produced according to Example I, infra, wherein the ratio of AROMOX ® DMMC-W:diisoamylene:base is either 0.8:0.2:99 or 1.8:0.2:98 and the weight ratio of DOWFAX ® 2A1:diisoamylene:base is 0.8:0.2:99 or 1.8:0.2:98 as described in Example XXI, infra.

THE INVENTION

It has now been determined that dimers of isoamylene produced according to the reaction:

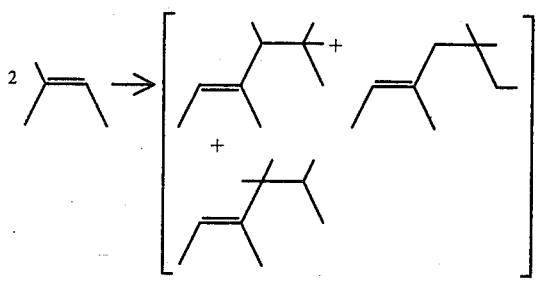

are capable of imparting or augmenting or enhancing a variety of fragrances in and to articles previously subjected to the bleaching action of aqueous hypochlorite bleach solutions by combining said dimers of isoamylene with the hypochlorite bleach solutions prior to treating the articles and also combining with the dimers of isoamylene and the hypochlorite bleach mixture, at least one compound defined according to the structure:

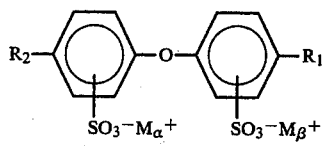

wherein at least one of $R_1$ and $R_2$ is $C_{10}$–$C_{12}$ branched or straight chain alkyl and when one of $R_1$ or $R_2$ is $C_{10}$–$C_{12}$ branched or straight chain alkyl the other of $R_1$ or $R_2$ is hydrogen and wherein $M_\alpha$ and $M_\beta$ are the same or different and each represents alkali metal, e.g. lithium, sodium or potassium.

Briefly, our invention contemplates augmenting or enhancing fragrances of articles which have been previously subjected to the action of aqueous hypochlorite bleaches by first admixing a potassium, sodium or lithium hypochlorite bleach solution (with which the said articles are to be ultimately treated) with a small but effective amount of at least one of the compounds defined according to the generic structure:

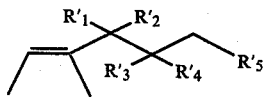

wherein $R_1'$, $R_2'$, $R_3'$, $R_4'$ and $R_5'$ are the same or different and each represents hydrogen or methyl with the provisos that (i) the sum total of the carbon atoms in $R_1'$, $R_2'$, $R_3'$, $R_4'$ and $R_5'$ 3; and (ii) $R_1'$ and $R_2'$ represents hydrogen when $R_5'$ represents methyl; and (iii) when either $R_1'$ or $R_2'$ is methyl, $R_5'$ is hydrogen.

More specifically, the structures of the compounds useful in practicing our invention are as follows:

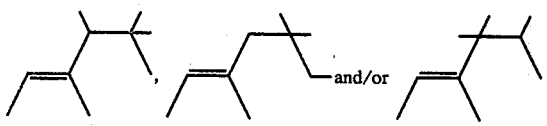

The diisoamylene compounds of our invention augment or enhance woody, piney and herbaceous aroma characteristics of articles previously treated with hypochlorite bleaches and also "cover" the aesthetically displeasing "hypochlorite-induced" aroma which is known to accompany such treated articles. Thus, in accordance with our invention, a hypochlorite bleach is admixed with an effective amount of diisoamylene derivative and in addition a stabilizing and emulsifying quantity of at least one compound defined according to the structure:

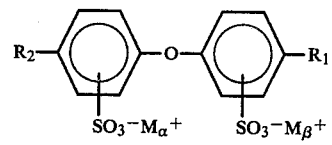

wherein at least one of $R_1$ or $R_2$ is $C_{10}$–$C_{12}$ branched or straight chain alkyl and when one of $R_1$ or $R_2$ is $C_{10}$–$C_{12}$ straight chain or branched chain alkyl the other of $R_1$ or $R_2$ is hydrogen and wherein $M_\alpha$ and $M_\beta$ are the same or different and each represent lithium, sodium or potassium.

The diisoamylene derivatives of our invention having the structures:

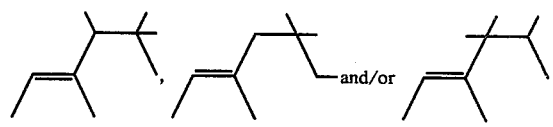

may be prepared by reacting 2-methyl-2-butene in the presence of an acidic catalyst which may be a Lewis acid such as, zinc chloride, aluminum chloride, aluminum bromide, diethyl aluminum chloride, diethyl aluminum bromide, ethyl aluminum dichloride, and diethyl aluminum bromide, boron trifluoride, boron trifluoride etherate, or any of the other catalysts enumerated in the following references:

i—Murphy & Lane, Ind. Eng. Chem., Prod. Res. Dev., Vol. 14, No. 3, 1975 p. 167 (Title: Oligomerization of 2-Methyl-2-Butene is Sulfuric and Sulfuric-Phosphoric Acid Mixtures).

ii—Whitmore & Mosher, Vol. 68, J. Am. Chem. Soc., February, 1946, p. 281 (Title: The depolymerization of 3,4,5,5-Tetramethyl-2-hexene and 3,5,5-Trimethyl-2-heptene in Relation to the Dimerization of Isoamylenes).

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II).

iv—U.S. Pat. No. 3,627,700, issued on Dec. 14, 1971, (Zuech)

v—U.S. Pat. No. 3,638,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2 p. 796 (Production of Di-isoamylene From Isoamylene Using Mercury Acetate Catalyst).

Depending upon the conditions of reaction, including temperature, pressure, mole ratio of 2-methyl-2-butene:-catalyst, concentration of 2-methyl-2-butene in solvent, concentration of catalyst in solvent and time of reaction, the ratio and nature of diisoamylene product isomers will vary in an as yet undetermined fashion. In any event, this invention comtemplates all isomers of diisoamylene defined according to the structures:

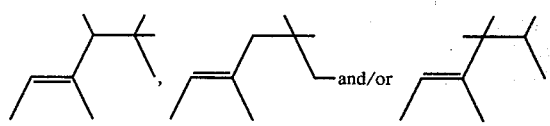

taken alone or in admixture in all proportions, when used in augmenting or enhancing the aroma of articles previously subjected to the bleaching action of hypochlorite bleaches such as aqueous solutions of lithium, sodium or potassium hypochlorite taken alone or in admixture.

As olfactory agents, the diisoamylene derivatives of our invention taken alone or in admixture, can be formulated into, or used as components of a "perfume composition" in conjunction with the hypochlorite bleaches and $C_{10}$–$C_{12}$ dialkyl diphenylether disulfonates.

The term "perfume composition" is used herein to mean a mixture of organic compounds including, for example, alcohols, aldehydes, ketones, nitriles, ethers, lactones, natural essential oils, synthetic essential oils and hydrocarbons other than the diisoamylene derivatives of our invention which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) top notes which are usually low boiling, fresh-smelling materials.

In perfume compositions, the individual component will contribute its particular olfactory characteristics, but the overall effect of the perfume composition will be (a) the sum of the effects of each of the ingredients and (b) in certain instances, a synergistic effect as a result of the addition of certain ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the diisoamylene derivatives of this invention which will be effective in perfume compositions depends on many factors, including the other ingredients, their amounts and the effects which are desired. It has been found that perfume compositions containing as little as 0.05% of the diisoamylene derivatives of this invention, or even less, can be used to impart an interesting, herbaceous, piney, woody aroma to articles previously treated with hypochlorite bleach compositions. The amount employed can range up to 70% or even higher, and will depend on considerations of cost, nature of the end product and the effect desired on the finished product and particular fragrance sought. Thus, for example, when fragrancing liquid bleach compositions containing alkali metal hypochlorite such as, for example sodium hypochlorite, for example CLOROX ® (registered trademark of CLOROX, Inc.), the amount employed can be as high as 100% of the fragrance used in the liquid bleach.

In addition, the perfume composition can contain a vehicle or carrier for the di-isoamylene derivatives, alone, or with other ingredients. The vehicle can be a liquid such as a non-toxic alcohol such as ethanol, a glycol such as propylene glycol, or the like. The carrier can be an absorbent solid, such as a gum or components for encapsulating the composition such as gelatin which can be used to form a capsule wall surrounding the perfume (produced by e.g. coacervation) when this solid is suspended in the hypochlorite bleach composition.

Thus, this invention relates to the production of also of perfumed single phase aqueous alkali metal hypochlorite solutions suitable for laundry and general domestic bleaching and sterilizing purposes. We have found that it is now possible to provide perfumed aqueous alkali metal hypochlorite solutions which yield a long lasting perfume aroma in the herbaceous, piney and woody area, and which are capable of imparting to surfaces (e.g. laundry and the hands of the user which are in direct contact with the hypochlorite solutions) to which they are applied a pleasant "herbaceous", "piney" and "woody" aroma and at the same time substantially diminishing or eliminating altogether the characteristic disagreeable "hypochlorite" aroma therefrom.

Accordingly, this invention consists of an aqueous solution of at least one alkali metal hypochlorite containing a stable perfume oil having as its main ingredient the aforementioned diisoamylene derivative and a surface active agent either consisting (i) solely of a $C_{10}$–$C_{12}$ alkyl diphenyl oxide dialkali metal sulfonate having the structure:

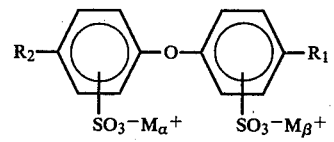

wherein at least of $R_1$ or $R_2$ is straight chain or branched chain $C_{10}$–$C_{12}$ alkyl and when one of $R_1$ or $R_2$ is straight chain or branched chain $C_{10}$–$C_{12}$ alkyl the other of $R_1$ or $R_2$ is hydrogen and wherein $M_\alpha$ and $M_\beta$ are the same or different and each is an alkali metal such as sodium, potassium or lithium; for example the compounds defined according to the structure:

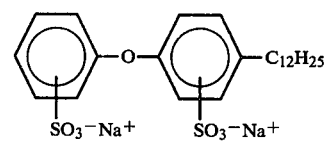

(wherein $C_{12}H_{25}$ represents several $C_{12}$ branched chain moieties) or the compounds defined according to the structure:

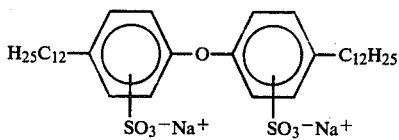

(wherein $C_{12}H_{25}$ represents several $C_{12}$ branched chain moieties) or the compounds defined according to the structure:

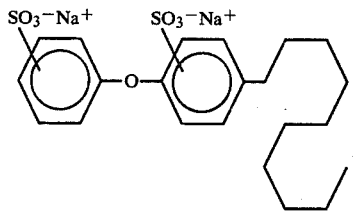

or the compounds defined according to the structure:

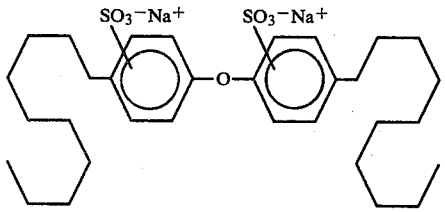

or mixtures of one or more of the foregoing compounds, or (ii) a mixture of at least one compound defined according to the generic structure:

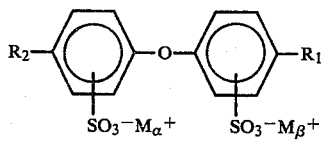

(wherein $R_1$, $R_2$, $M_\alpha$ and $M_\beta$ are defined supra) and an amine oxide composition consisting essentially of one or more morpholine and/or dimethyl $C_{11}$-$C_{13}$ straight chain alkyl amine oxide having the generic structure:

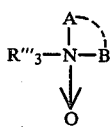

in an amount greater than 55% of said amine oxide composition wherein $R_3'''$ is straight chain alkyl having from 11 up to 13 carbon atoms and A and B are each separately methyl, or taken together, complete a morpholino ring and having a pH in the range of 11–14.0.

The chain lengths of the $R_3'''$ moiety (or moieties) of the predominating alkyl dimethyl amine oxides of the amine oxide composition aides in providing for an aqueous hypochlorite bleach or sterilizing solution which can be perfumed in the "woody", "piney" and "herbaceous" aroma formulations required for our invention, but the compound having the structure:

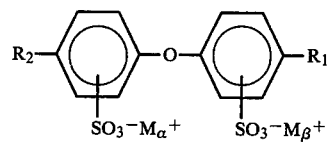

or mixture of such compounds taken alone or taken further together with the alkyl dimethyl amine oxide composition will aid even further in providing such a perfume hypochlorite bleach formulation and the compounds defined according to the structure:

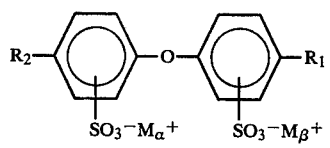

as stated above may be used alone.

The concentration of the composition of matter consisting essentially of the compounds having the structure:

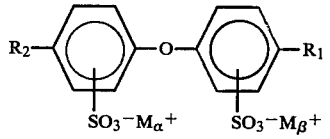

(wherein $R_1$, $R_2$, $M_\alpha$ and $M_\beta$ are defined supra) taken alone or taken in admixture with the amine oxide composition required to create the transparent liquid phase or gel phase solution of this invention is from 0.10% up to 2.0% based on the total weight of solution. Concentrations of diphenyl oxide derivatives less than 0.10% or mixtures of diphenyl oxide derivatives and amine oxides of less than 0.10% will not give rise to the desired single liquid or gel phase system containing the desired special perfume oil consisting essentially of one or more diisoamylene isomers having hervaceous, piney and/or woody aroma profiles required for this invention. From a commercial standpoint the concentration of $C_{10}$-$C_{12}$ straight chain or branched chain alkyl substituted diphenyl oxide dialkali metal sulfonate (hereinafter referred to as "diphenyl oxide derivative") taken alone or taken in conjunction with amine oxide greater than 2.0% based on the total weight of hypochlorite solution are not needed and give rise to unnecessary costs.

The pH range of the aqueous alkali metal hypochlorite solution containing the diphenyl oxide derivative composition defined according to the structure:

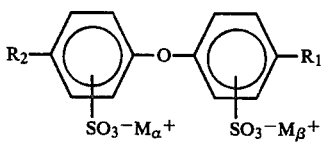

taken alone or in conjunction with the amine oxide composition having the structure:

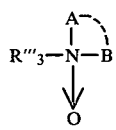

and one of the requisite perfume formulations consisting essentially of one or more of the diisoamylene derivatives of our invention which are stable to aqueous hypochlorite and which are capable of yielding and imparting the desired and required overall herbaceous, piney and woody fragrance impression is critical; that is, a pH of from 11 up to 14.0 is required for the composition of our invention, with a preferred pH range being between 12.0 and 13.1. The requisite pH range is achieved by adding an aqueous solution of alkali metal hydroxide (e.g. from 1 molar up to 12.5 molar) to the alkali metal hypochlorite solution which has or will have added to it the $C_{10}$–$C_{12}$ straight or branched chain alkyl substituted diphenyl oxide dialkali metal sulfonate-diisoamylene perfume oil premix or the $C_{10}$–$C_{12}$ straight or branched chain alkyl substituted diphenyl oxide dialkali metal sulfonateamine oxide-diisoamylene-containing perfume oil premix.

The percentage of diisoamylene-containing perfume oil or diisoamylene per se having the properties which yield herbaceous, piney or woody aromas is in the range of from 0.01% up to 0.8% based on the total final weight of alkali metal hypochlorite solution. Lower concentrations of such perfume oils will not be adequate to give rise to the desired subtantital diminution or elimination of the characteristic disagreeable hypochlorite aroma (which exists on, for example, laundry and/or the hands of the individual user which have been in direct contact with the hypochlorite bleach or sterilizing solution subsequent to the use of aqueous hypochlorite solutions as a general domestic bleach or sterilizer). Quantities of perfume oil greater than 0.8% have been found to be uneconomical and unnecessary for the practice of our invention, although, in the case of using the diisoamylene derivatives of our invention as aromatizing agents (without any additional adjuvants) the very low cost of the diisoamylene and very high stability of the diisoamylene give rise to a very commercial economical use even at very high levels.

Several processes may be used in order to produce a hypochlorite bleaching or sterilizing solution whereby the desired herbaceous, piney and woody aroma profiles are imparted to the articles treated with said hypochlorite solutions. Thus, for example, the diisoamylene-containing perfume oil may be premix with the diphenyl oxide derivative or the diphenyl oxide derivative-amine oxide solubilizer-stabilizer (having the structures, respectively:

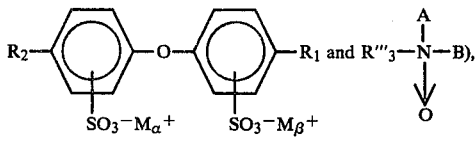

and the resulting perfume oil-diphenyl oxide derivative or perfume oil-diphenyl oxide derivative-amine oxide premix is then mixed with the hypochlorite bleaching or stirilizing solution with stirring. Immediately after such addition, an aqueous alkali metal hydroxide solution is added to the mixture to bring the pH to the range of 11–14.0. A pH of less than 11 is not desired since it is difficult to achieve a single phase stable system at such low pH's. A pH higher than 14.0 will also create a system which is (1) is unnecessarily corrosive; (2) will narrow the range of perfume oils usable in conjunction with diisoamylene in the system; and (3) will limit the particular ingredients usable in such perfume oils in conjunction with the diisoamylenes. On the other hand, if the diisoamylene are used alone, a pH of 14.0 is acceptable.

The aqueous alkali metal hydroxide can be added to the aqueous alkali metal hypochlorite solution before adding the diphenyl oxide derivative (taken alone or in conjunction with the amine oxide) or the diisoamylene or the diisoamylene-containing perfume oil. Indeed, the ingredients: the diisoamylene or diisoamylene-containing perfume oil; the alkali metal hydroxide and the diphenyl oxide drivative or the diphenyl oxide derivative-amine oxide composition (having the structures respectively:

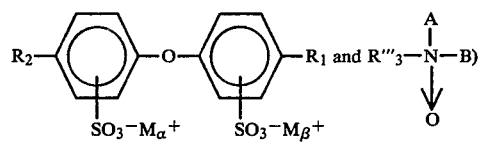

may be added or admixed in any order which is convenient to the formulator. One desirable process involves first forming the diphenyl oxide derivative or dipheny oxide derivative-amine oxide composition-diisoamylene or diisoamylene-containing perfume oil "premix", mixing the premix with the alkali metal hypochlorite solution and finally adjusting the pH of the solution with alkali metal hydroxide to bring the pH to within the range of 11–14.0. A second, more preferable process, involves first adjusting the pH of the aqueous alkali metal hypochlorite solution to 11–14.0 and then admixing the solution with the afore-described "premix".

The alkali metal hypochlorites preferred in the practice of our invention are: sodium hypochlorite, potassium hypochlorite and lithium hypochlorite or mixtures of same. The alkali metal hydroxides preferred in the practice of this invention are: lithium hydroxide, potassium hydroxide and sodium hydroxide or, if desired, mixtures of such hydroxides.

The temperature at which the composition of our invention remains both substantially stable and commercially useful for the purposes set forth herein (that is, remains as a clear single aqueous or gel phase and retains (1) the desired properties inherent in the known bleaching and sterilizing uses of aqueous alkali metal hypochlorite liquid or gel solutions, and (2) the properties imparted thereto as a result of the diisoamylene derivatives or diisoamylene-containing perfume oils which impart to articles previously subjected to the aqueous alkali metal hypochlorite gel or liquid solutions a herbaceous, piney and/or woody aroma profile, varies from approximately 20° F. up to approximately 120° F. At temperatures below 20° F. a two-phase system usually occurs and at temperatures higher than 120° F. the bleaching or sterilizing efficiency of the compositions of our invention is diminished at an excessive rate.

When it is desired to (1) initially form the $C_{10}$–$C_{12}$ straight chain or branched chain diphenyl oxide alkali metal sulfonate or diphenyl oxide derivative-amine oxide-diisoamylene or diisoamylene-containing perfume oil premix (which is in the gel phase or the liquid phase); (2) then combine the resulting premix with an aqueous alkali metal hypochlorite solution and then (3) adjust the pH of the resulting solution to the range of 11–14.0, then the following temperature of mixing ranges are considered to be within the scope of this invention:

(a) Formation of the diphenyl oxide derivative or diphenyl oxide-amine oxide-diisoamylene or diisoamylene-containing perfume oil premix: 20° F.–150° F.

(b) Mixing of the premix with aqueous metal alkali hypochlorite solution: 20° F.–120° F.

(c) Adjustment of pH of solution to the range of 11–14.0 using aqueous alkali metal hydroxide solution: 20° F.–120° F.

In any event, wherever a mixing unit operation involves the aqueous alkali metal hypochlorite solution, the temperature of mixing is limited to the range of 20° F.–120° F. Where the mixing unit operation involves the mixing of a diisoamylene or diisoamylene-containing perfume oil, the upper bound of the temperature range is limited by the stability of the least stable ingredient in the diisoamylene composition of matter or diisoamylene-containing perfume oil usable in the practice of our invention; and the lower bound of said temperature range is limited by the least temperature where a single liquid phase or gel phase including the perfume oil will exist. Where a unit mixing operation of the process of our invention involves the mixing of one or more diphenyl oxide derivatives having the generic structure:

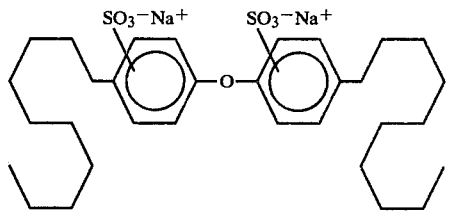

taken alone or taken together with one or more amine oxides having the generic structure:

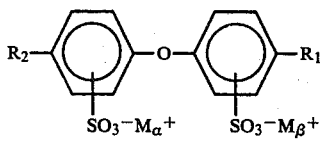

and compounds defined according to the structure:

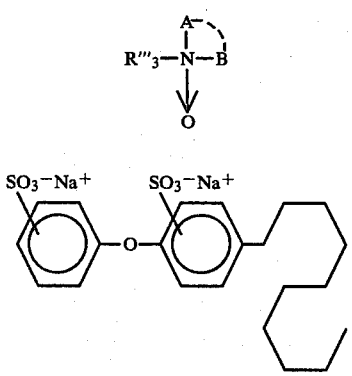

otherwise known as DOWFAX® 2A1 in the case where $R_1$ or $R_2$ represents branched $C_{12}H_{25}$ alkyl chains and the other of $R_1$ or $R_2$ represents hydrogen, or DOWFAX® 3B2 in the case where $R_1$ or $R_2$ represents a straight $C_{10}$ alkyl chain and the other of $R_1$ or $R_2$ represents hydrogen (DOWFAX® being a registered trademark of the Dow Chemical Company of Midland, Mich.).

When used in conjunction with the diphenyl oxide derivatives, preferred amine oxide compositions, from a practical standpoint, useful in the practice of our invention are the commercially available (1) dimethyl "cocoamine" oxide (a mixture which is dominated by dimethyl-$C_{12}$–$C_{16}$ straight chain alkyl amine oxides; more particularly a mixture containing approximately 70% $C_{12}$ straight chain alkyl amine oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$–$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: Aromox® DMC-W and Aromox® DMMC-W which are 30% aqueous dimethyl cocoamine oxide solutions and Aromox® NCMDW which is a 40% aqueous N-cocomorpholine oxide solution, each of which is produced by the Armac Division of AKZO of Chicago, Ill. These materials are described in Brochure 68011, published by Armour Industrial Chemicals, P.O.B. 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative-amine oxide-diisoamylene or diisoamylene-containing perfume oil compositions covered by our invention. The usual percent of alkali metal hypochlorite in solution is about 5%, the percentage of sodium hypochlorite in such materials as CLOROX® the registered trademark of Clorox Corporation.

As stated above, the diisoamylene or diisoamylene-containing perfume oil used in conjunction with the aqueous alkali metal hypochlorite solution must have such properties as to be able (1) to impart to the resulting "aqueous alkali metal hypochlorite" liquid or gel solution either a "herbaceous" or "piney" or "woody" aroma or combination thereof; (2) to effect a substantial diminution or elimination of the disagreeable "hypochlorite" aroma which is imparted to surfaces (e.g. bleached laundry or the hands of the user which are in direct contact with the hypochlorite solution) on which known aqueous alkali metal hypochlorite solutions have been used; and (3) to impart to the surfaces with which such aqueous alkali metal hypochlorite solutions are in contact, a pleasant long lasting stable herbaceous, piney and/or woody aroma. Examples of ingredients usable and suitable for the aforementioned purposes, that is usable in conjunction with the diisoamylenes and usable in conjunction with the hypochlorites and diphenyl oxide derivatives of our invention are as follows:

a. Material Useful for Adding in Imparting a "Woody" Aroma:
 1. Cedryl alkyl ethers covered by U.S. Pat. No. 3,373,208 such as cedryl methyl ether;
 2. Isochroman musks covered by U.S. Pat. Nos. 3,360,530 and 3,591,528 such as 6-oxa-1,1,3,3,8-pentamethyl-2,3,5,6,7,8-hexahydro-1H-benz(f)indene;
 3. Polycyclic ethers covered by U.S. Pat. No. 3,281,432, such as octahydro-1,3a,6-trimethyl-1H-1,6a,ethanopentaleno-(1,2-C)furan;
 4. Polycyclic ketones such as hexahydro-1,1,5,5-tetramethyl-2H-2,4a-methanonaphthalen-8-(5H)one.

b. Materials Useful for Aiding in Imparting a "Herbaceous" Aroma:
 1. Indane musks covered by U.S. Pat. No. 2,889,367 such as 4-acetyl-1,1-dimethyl-6-t-butyl indane;
 2. Naphthyl ethers such as $\beta$-naphthyl methyl ether and $\beta$-naphthyl ethyl ether;
 3. Cyclohexyl ethyl ether;
 4. Aryl alkanones as described in Canadian Pat. No. 780,489 such as 2,5-dimethyl-5-phenylhexanone-3.

c. Materials Useful for Imparting a "Piney" Aroma:
 1. "Pinoacetaldehyde" prepared according to U.S. Pat. No. 3,636,113
 2. Polycyclic alkanone derivatives prepared according to U.S. Pat. No. 4,076,853.

It will be understood that a number of materials which impart herbaceous, piney and woody aromas will not be useful for use in our invention because they are interalia, easily oxidized by the alkali metal hypochlorite in the system. Examples are 1,5,9-trimethyl-12-acetyl-cyclododecatreiene-1,5,8 and 1,5,9-trimethyl-12-cyclododecadiene-1,8 covered by British Pat. No. 1,204,409.

A basic feature of our invention concerns the fact that the only detergent group needed or desirable in the composition of our invention is the class of diphenyl oxides defined according to the structure:

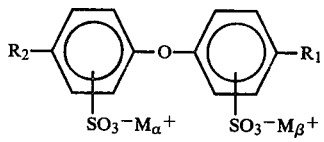

wherein $R_1$, $R_2$, $M_\alpha$ and $M_{62}$ are defined supra, taken alone or in conjunction with the class of morpholino and/or dimethyl $C_{11}$-$C_{13}$ straight chain alkyl amine oxides defined according to the structure:

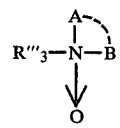

More specifically, such detergents as sodium decyl ether sulfate, sodium myristyl ether sulfate, sodium lauryl ether sulfate and lithium lauryl ether sulfate are neither desired nor are they required. Furthermore the well known hydrotropes employed in prior art compositions such as the well known family of clarifying agents comprising the alkali metal or alkali earth metal salts of mono- and polyalkylated benzene or naphthalene sulfonates such as sodium xylene or magnasium toluene sulfonate are again neither desired nor are they required in the compositions intended to be encompassed by the instant invention.

Another basic feature of our invention concerns the fact that when it is desired to have a gel phase composition, thickener agents may be employed in conjunction with the system of hypochlorite bleach-diisoamylene or diisoamylene-containing perfume-diphenyl oxide derivative or diphenyl oxide derivative-amine oxide (having the structure:

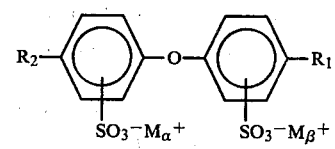

and having the structure:

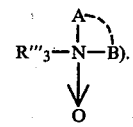

of our invention.

Furthermore, a gel may be formed by adding to the "premix" a thickener agent where the premix contains the diisoamylene or disoamylene-containing perfume as well as the diphenyl oxide derivative or diphenyl oxide derivative-amine oxide derivative.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is in addition to being in a semi-solid state unobviously, advantageously and unexpectedly stable over long periods of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on overall weight of hypochlorite bleach-diphenyl oxide derivative or diphenyl oxide derivative-amine oxide-diisoamylene or diisoamylene-containing perfume composition of our invention. By the same token, the percentages of thickening agents as stated above, which may be used in thickened premix compositions of our invention are from about 5% by weight up to about 60% by weight of thickener based on overall weight of premix which is diphenyl oxide derivative or diphenyl oxide derivative-amine oxide-diisoamylene or diisoamylene containing perfume composition of our invention.

The following examples are given to illustrate embodiments of the invention as it is now preferred to practice it. It will be understood that these examples are illustrative and the invention is not to be considered as

EXAMPLE I

Preparation of Di-isoamylene Derivatives

Reaction:

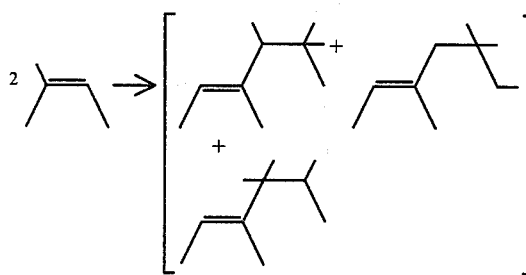

Di-isoamylene is prepared according to one of the procedures set forth in the following references:

i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).

ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)

iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)

iv—U.S. Pat. No. 3,627,700, issued on Dec. 14, 1971, (Zuech)

v—U.S. Pat. No. 3,538,181, issued on Nov. 3, 1970, (Banks)

vi—U.S. Pat. No. 3,461,184, issued on Aug. 12, 1969 (Hay, et al)

vii—Gurwitsch, Chemische Berichte, 1912, Vol. 2, p. 796 (Production of Di-isoamylene From Isoamylene Using Mercury Acetate Catalyst)

As an illustration, and not by way of limitation, the following Example sets forth the preparation of di-isoamylenes useful in producing the fragrances of our invention:

Over a period of ten hours, 2-methyl-2-butene is pumped through a 5'×⅝ (0.625 inch) tube packed with 15.0 g of polystyrene sulfonic acid catalyst, at a temperature of 100° C. and at a pressure of 400 psig.

The resulting material was distilled in a fractionation column in order to separate the di-isoamylene from the higher molecular weight polymers, which are formed during the reaction as by-products.

Figure 1A:
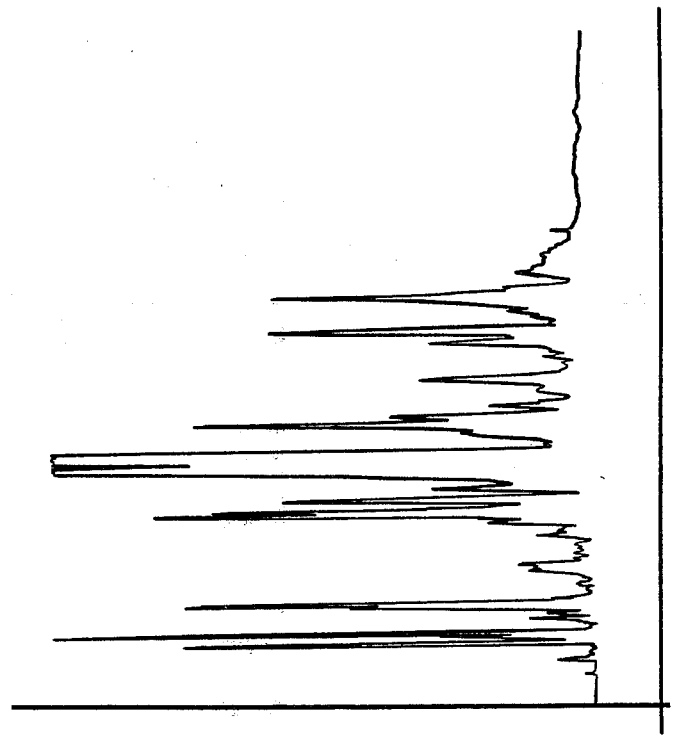
FIG. 1A represents the GLC profile for the reaction product of Example I using a 70% sulfuric acid catalyst at 35° C.

FIG. 1A represents the GLC profile for the reaction product of Example I using a 70% sulfuric acid catalyst at 35° C.

Figure 1B:
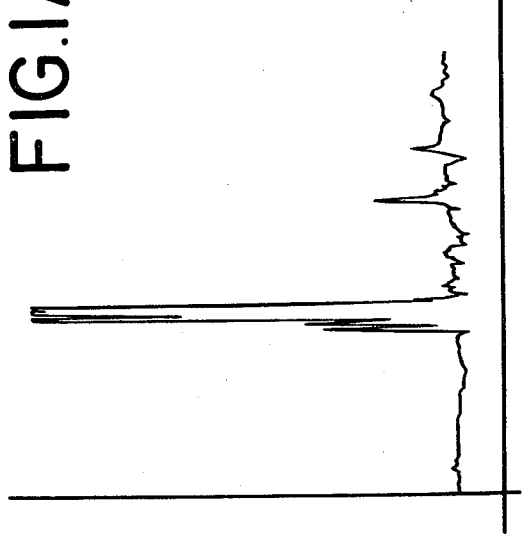
FIG. 1B represents the GLC profile for the reaction product of Example I using an Amberlyst ® 15 acidic ion exchange resin catalyst at a temperature of 150° C.

FIG. 1B represents the GLC profile for the reaction product of Example I using an Amberlyst ® 15 acetic ion exchange resin catalyst at a temperature of 150° C.

Figure 1C:
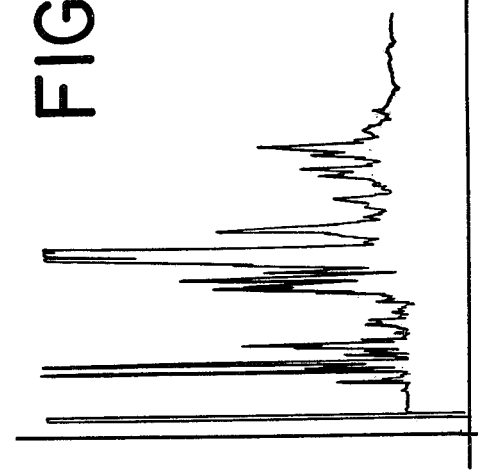
FIG. 1C represents the GLC profile for the reaction product of Example I, using an Amberlyst ® 15 catalyst at 100° C.

FIG. 1C represents the GLC profile for the reaction product of Example I, using an Amberlyst ® 15 catalyst at 100° C.

Figure 1E:
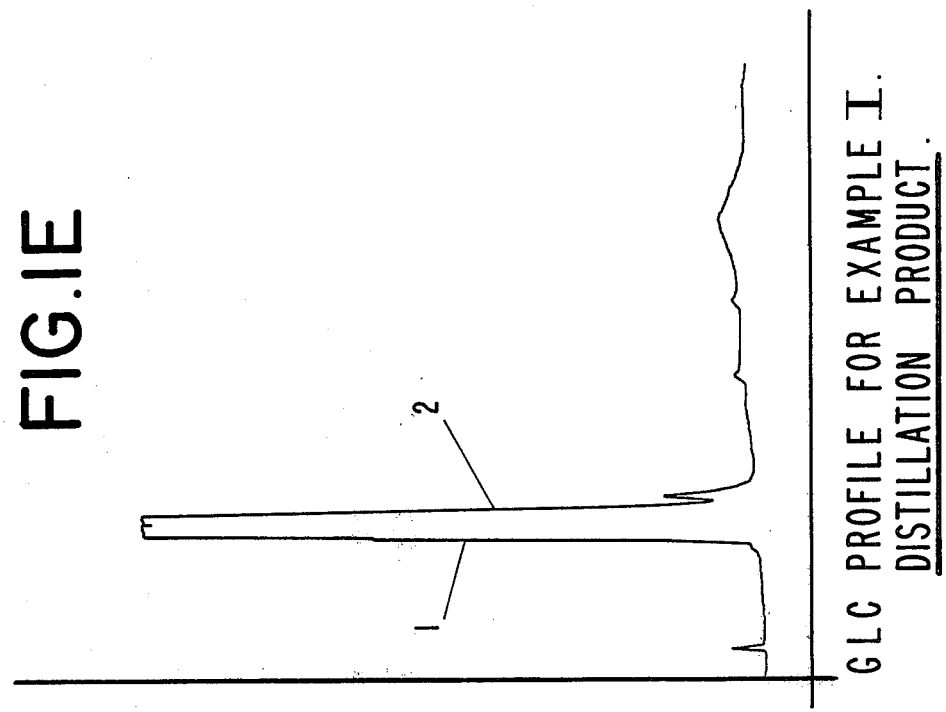
FIG. 1E represents the GLC profile for the reaction product of Example I, using a sulfuric acid catalyst, at 35° C. and an alpha-methylstyrene diluent according to the conditions of United Kingdom Patent Specification No. 796,130 (distilled reaction product).
Figure 1D:
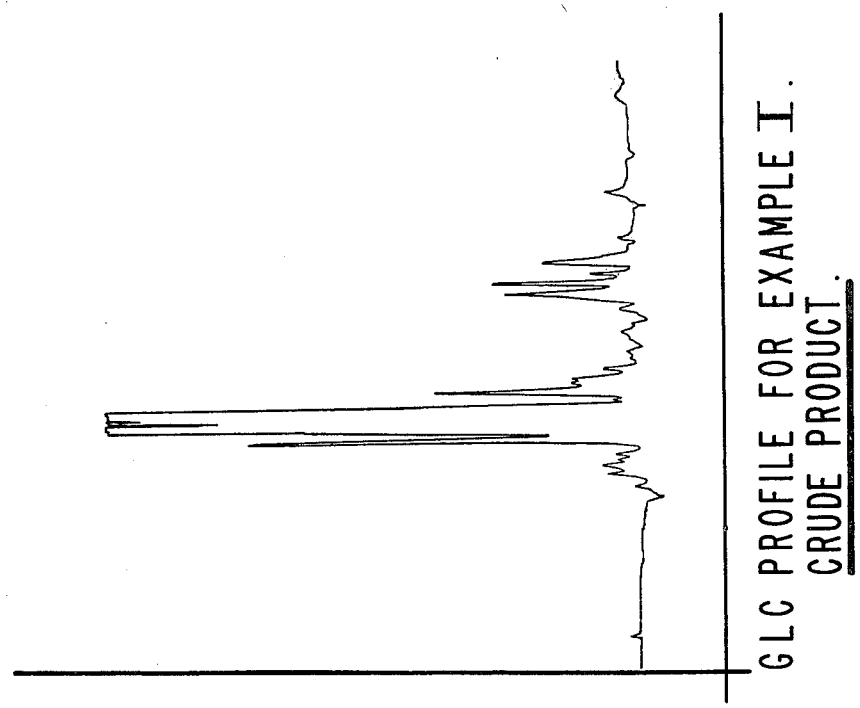
FIG. 1D represents the GLC profile for the reaction product of Example I, using a sulfuric acid catalyst and an alpha-methylstyrene diluent at 35° C. according to the conditions of United Kingdom Patent Specification No. 796,130 (crude reaction product)

FIG. 1D represents the GLC profile for the reaction product of Example I, using a sulfuric acid catalyst and an alpha-methylstyrene diluent at 35° C. according to the conditions of United Kingdom Patent Specification No. 796,130 (crude reaction product).

FIG. 1E represents the GLC profile for the reaction product of Example I, using a sulfuric acid catalyst, at 35° C. and an alpha-methylstyrene diluent according to the conditions of United Kingdom Patent Specification No. 796,130 (distilled reaction product).

Figure 2A:
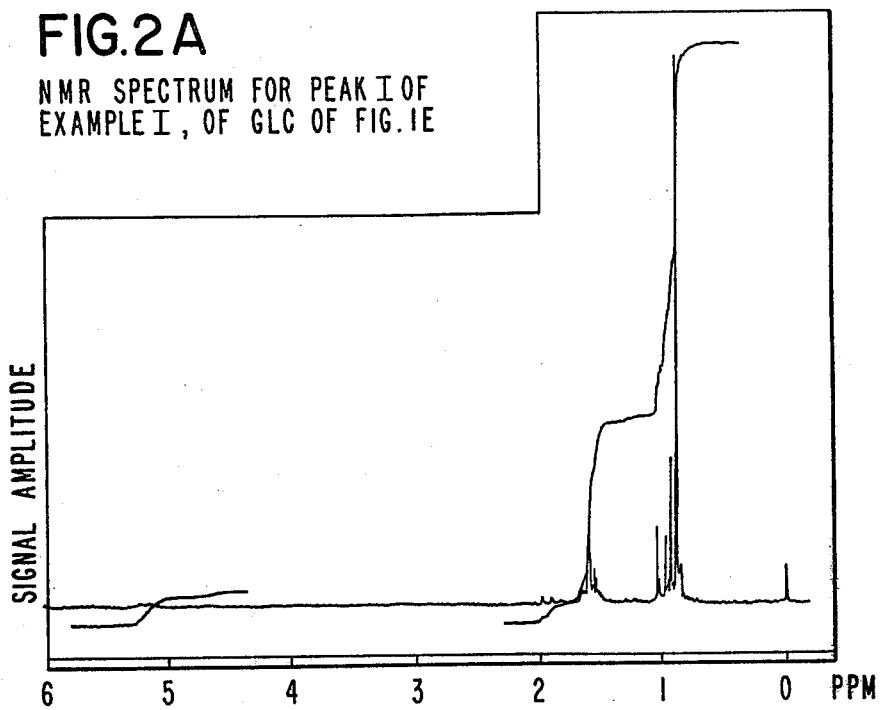
FIG. 2A represents the NMR spectrum for Peak 1 of the GLC profile of FIG. 1E.

FIG. 2A represents the NMR spectrum for Peak 1 of the GLC profile of FIG. 1E. Peak 1 has been determined by analysis to be the compound having the structure:

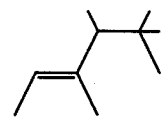

Figure 2B:
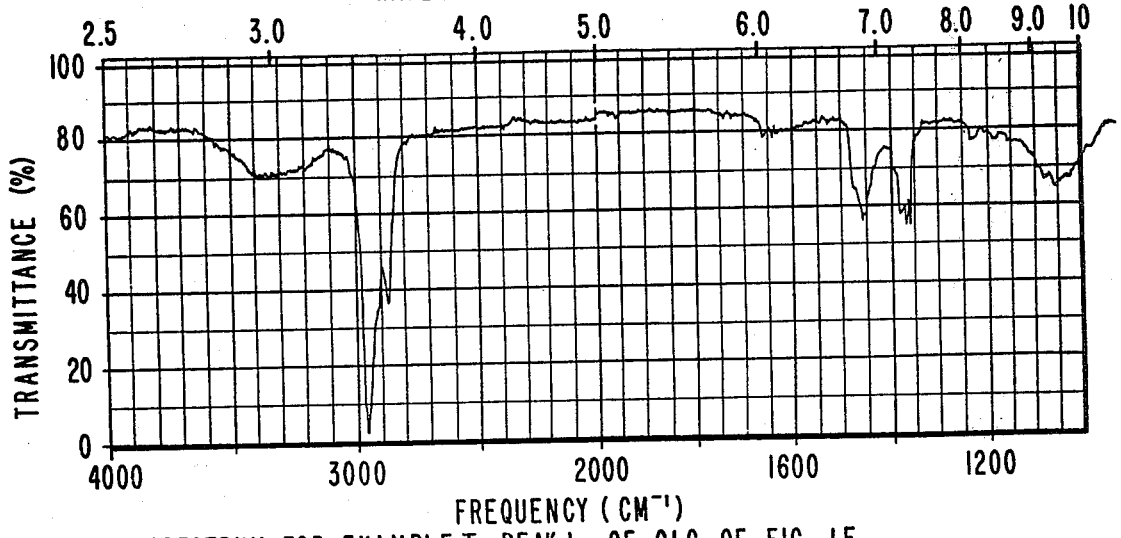
FIG. 2B represents the infra-red spectrum for Peak 1 of the GLC profile of FIG. 1E.

FIG. 2B represents the infra-red spectrum for Peak 1 of the GLC profile of FIG. 1E.

Figure 3A:
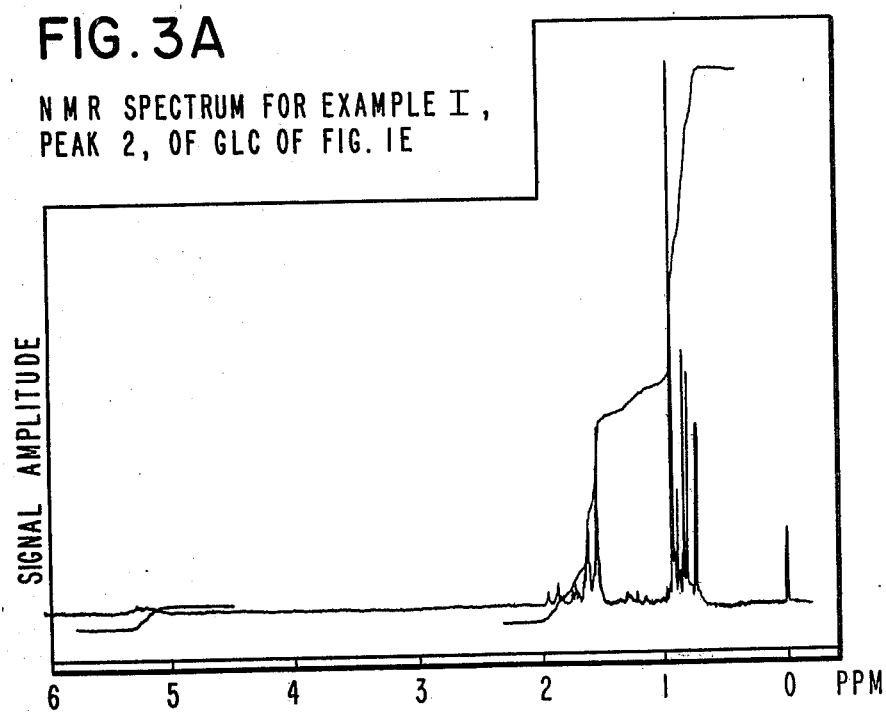
FIG. 3A represents the NMR spectrum for Peak 2 of the GLC profile of FIG. 1E.

FIG. 3A represents the NMR spectrum for Peak 2 of the GLC profile of FIG. 1E. Peak 2 contains compounds having the structures:

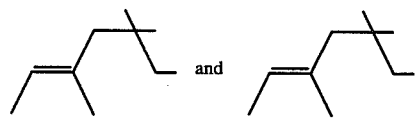

Figure 3B:
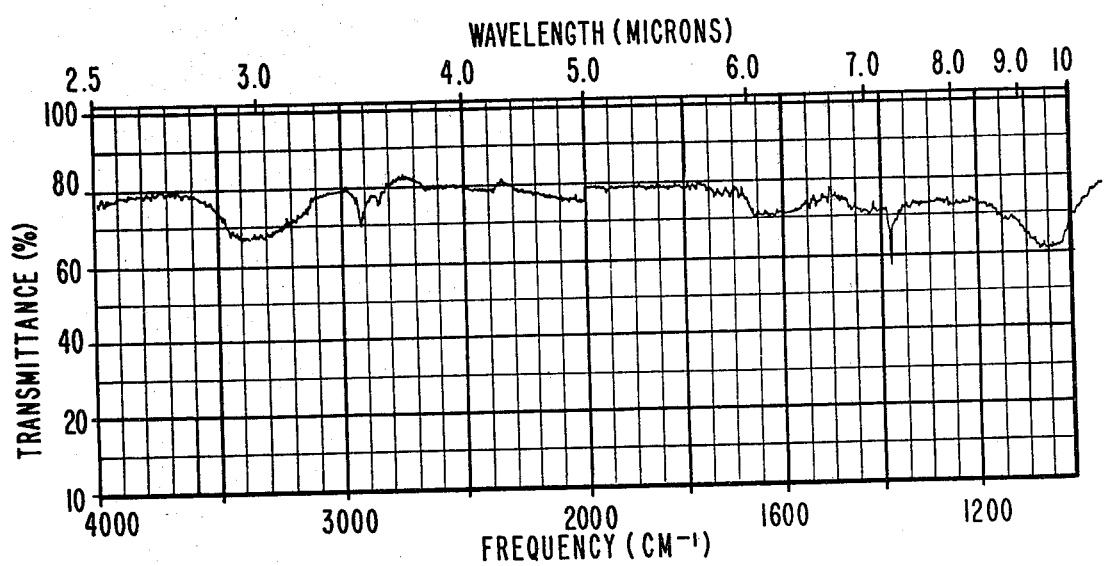
FIG. 3B represents the infra-red spectrum for Peak 2 of the GLC profile of FIG. 1E.

FIG. 3B represents the infra-red spectrum for Peak 2 of the GLC profile of FIG. 1E.

Figure 4:
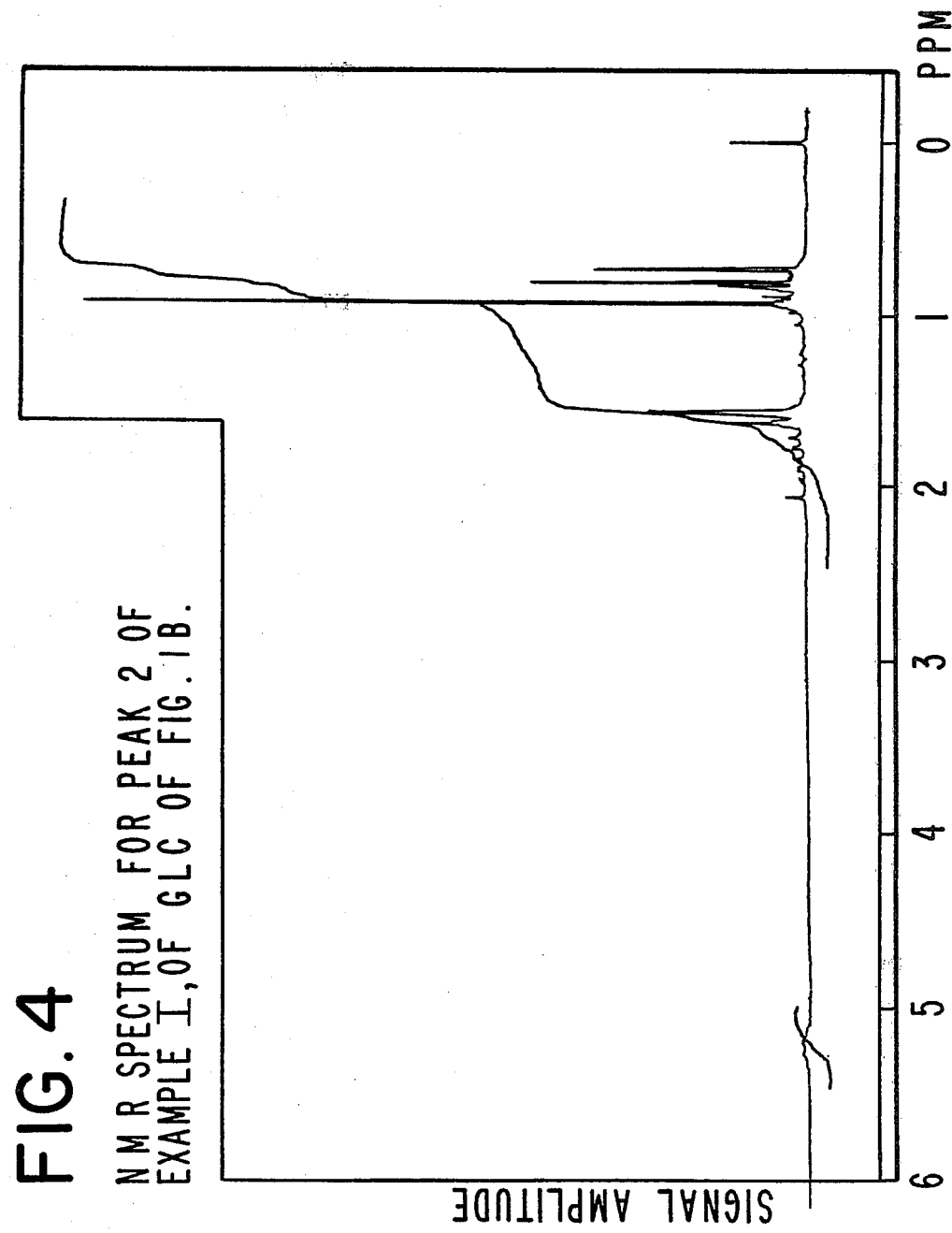
FIG. 4 represents the NMR spectrum for Peak 2 of the GLC profile of FIG. 1B.

FIG. 4 represents the NMR spectrum for Peak 2 of the GLC profile of FIG. 1B.

EXAMPLE II

The di-isoamylene produced according to Example I has a woody, piney, herbaceous note which may be utilized to a great extent in inexpensive functional products. The following pine fragrance demonstrates the use of this material in perfume compositions. In this case it is used as 47.9%.

| | |
|---|---|
| Di-isoamylene | 479 |
| Isobornyl Acetate | 100 |
| Camphor | 10 |
| Terpineol | 25 |
| Fir Balsam Absolute (50% in Diethyl Phthalate | 20 |
| Coumarin | 4 |
| Linalool | 30 |
| Anethol | 2 |
| Fenchyl Alcohol | 10 |
| Lemon Terpenes Washed | 50 |
| Borneol | 5 |
| Galbanum Oil | 5 |
| Turpentine Russian | 150 |
| Pinus Pumilionus | 50 |
| Eucalyptol | 50 |
| 2,2,6-trimethyl-1-cyclohexene-1-carboxaldehyde | 5 |
| Maltol 1% in Diethyl Phthalate | 5 |

The presence of the di-isoamylene supports the pine notes and produces a considerable savings in the cost of the formulation.

EXAMPLE III

Preparation of a Cosmetic Powder Composition

A cosmetic powder is prepared by mixing in a ball mill, 100 g of talcum powder with 0.25 g of the perfume composition prepared according to Example II. It has an excellent, piney aroma with woody and herbaceous nuances.

EXAMPLE IV

Perfumed Liquid Detergent

Concentrated liquid detergents (Lysine salt of n-dodecylbenzene sulfonic acid as more specifically described in U.S. Pat. No. 3,948,818, issued on Apr. 6, 1976) with herbaceous, woody and piney aroma nuances are prepared containing 0.10%, 0.15%, 0.20%, 0.25%, 0.30% and 0.35% of the fragrance prepared according to Example II. They are prepared by adding and homogeneously mixing the appropriate quantity of fragrance formulation prepared according to Example II in the liquid detergent. The detergents all possess excellent piney aromas with woody and herbaceous undertones, the intensity increasing with greater concentrations of perfume composition of Example II.

EXAMPLE V

Preparation of a Cologne and Handkerchief Perfume

The composition prepared according to Example II is incorporated into a cologne at concentrations of 2.0%, 2.5%, 3.0%, 3.5%, 4.0%, 4.5% and 5.0% in 85% aqueous food grade ethanol; and into a handkerchief perfume at concentrations of 15%, 20%, 25% and 30% (in 95% aqueous food grade ethanol). A distinctive and definite herbaceous, woody, piney aroma is imparted to the cologne and to the handkerchief perfume at all levels indicated above.

EXAMPLE VI

Preparation of Soap Composition

One hundred grams of soap chips (IVORY ®, produced by the Procter & Gamble Company, Cinncinati, Ohio) are mixed with one gram of the formulation of Example II until homogeneous compositions are obtained. In each of the cases, the homogeneous compositions are heated under three atmospheric pressure at 180° C. for a period of three hours and the resulting liquids are placed into soap molds. The resulting soap cakes, on cooling, manifest excellent herbaceous, woody and piney aromas with an emphasis on the piney aspects of the aroma.

EXAMPLE VII

Preparation of a Solid Detergent Composition

A detergent is prepared from the following ingredients according to Example 1 of Canadian Pat. No. 1,007,948:

| Ingredient | Percent by Weight |
| --- | --- |
| "Neodol ® 45-11 (a $C_{14}$-$C_{15}$ Alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.10, 0.15, 0.20 and 0.25 grams of the pine perfume of Example II. The detergent sample has an excellent herbaceous, woody and piney aroma.

EXAMPLE VIII

Preparation of a Cosmetic Powder Composition

A cosmetic powder is prepared by admixing in a ball mill, 100 g of talcum powder with 0.25 g of one of the di-isoamylene compounds prepared according to Example I. The resulting cosmetic powder has an excellent herbaceous, piney and woody aroma.

EXAMPLE IX

Perfumed Liquid Detergent

Concentrated liquid detergents (Lysine salt of n-dodecylbenzene sulfonic acid as more specifically described in U.S. Pat. No. 3,948,818, issued on Apr. 6, 1976) with herbaceous, woody and piney aroma notes are prepared containing 0.10%, 0.15%, 0.20% and 0.25% of one or more of the di-isoamylenes prepared according to Example I. They are prepared by adding and homogeneously mixing the appropriate quantity of di-isoamylene composition in the liquid detergent. The detergents all possess piney, woody and herbaceous nuances, the intensity of each characteristic increasing with greater concentrations of di-isoamylene composition of Example I.

EXAMPLE X

Preparation of Colognes and Handkerchief Perfumes

The di-isoamylene derivatives prepared according to Example I are incorporated into colognes at concentrations of 2.0%, 2.5%, 3.0%, 3.5%, 4.0% and 4.5% in 85% aqueous food grade ethanol; and into handkerchief perfumes at concentrations of 15%, 20%, 25% and 30% (in 95% aqueous ethanol). Distinctive herbaceous, woody and piney nuances are imparted to the colognes and to the handkerchief perfumes at various levels indicated above.

EXAMPLE XI

Utilizing the procedure of Example I of column 15 of U.S. Pat. No. 3,632,396, a nonwoven cloth substrate useful as a dryer-added fabric-softening article of manufacture prepared wherein the substrate, the substrate coating and the outer coating and the perfuming material are as follows:

1. a water "dissolvable" paper ("Dissolvo Paper").
2. Adogen 448 (m.p. about 140° F.) as the substrate coating; and
3. An outer coating having the following formulation (m.p. about 150° F.):
   57 percent $C_{20-22}$ HAPS
   22 percent isopropyl alcohol
   20 percent antistatic agent
   1 percent of one or more of the di-isoamylene derivatives of Example I.

Fabric-softening compositions prepared according to Example I having woody, piney and herbaceous aroma characteristics essentially consist of a substrate having a weight of about 3 grams per 100 square inches of substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The woody, herbaceous and piney aroma is imparted in a pleasant manner to the head space in the dryer on operation thereof, using the said dryer-added fabric softening nonwoven fabric.

In the following examples, Aromox ® DMC-W and Aromox ® DMMC-W are 30% aqueous solutions of dimethyl cocoamine oxide; and Aromox ® NCMDW is a 40% aqueous solution of N-cocomorpholine oxide produced by Armac Division of AKZO of Chicago, Ill.

EXAMPLE XII

Four drops of one of the di-isoamylene compositions prepared according to Example I is added to two grams of Aromox ® DMC-W to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody/piney/herbaceous" aroma. Furthermore, no such characteristic "hypochlorite" aroma is retained on the hands of the individual handling such laundry in both the wet and the dry states.

EXAMPLE XIII

Aromox ® DMMC-W in various quantities is mixed with 0.1 gram of one of the di-isoamylene compositions prepared according to Example I. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When used as laundry bleaches, the resulting bleached laundries on dry-out in an atmosphere of 50% relative humidity in each of the three cases above retain a "clean fresh", "woody", "herbaceous", "piney" aroma whereas without the use of the diisoamylene materials prepared according to Example I, the bleached laundry has a faint characteristic disagreeable hypochlorite aroma.

EXAMPLE XIV

Two grams of Aromox ® DMMC-W is admixed with eight drops of one of the di-isoamylene compositions of Example I. The premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of 1 week. The resulting solution remains clear in a single phase. When used as a laundry bleach, the resulting bleached laundry on dry-out in an atmosphere of 50% relative humidity retains a "clean fresh" woody, herbaceous, piney aroma; whereas without the use of the di-isoamylene prepared according to Example I, the bleached laundry has a faint characteristic disagreeable "hypochlorite" aroma.

EXAMPLE XV

Two grams of Aromox ® DMMC-W is admixed with eight drops of one of the di-isoamylene compositions of Example I. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh", woody, herbaceous, piney aroma; whereas without the use of the di-isoamylene prepared according to Example I, the bleached laundry has a faint characteristic disagreeable "hypochlorite" aroma.

EXAMPLE XVI

Two grams of Aromox ® DMMC-W is admixed with eight drops of one of the di-isoamylene products produced according to Example I. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting bleached laundry, on dry-out in an atmosphere of 50% relative humidity, retains a "woody, herbaceous, piney" aroma whereas without the use of the di-isoamylene composition of Example I, the bleached laundry has a faint characteristic disagreeable "hypochlorite" aroma.

EXAMPLE XVII

Four drops of one of the di-isoamylene mixtures produced according to Example I, is added to 1.5 grams of Aromox ® NCMDW to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XVIII

Four drops of one of the di-isoamylene mixtures produced according to Example I, is added to 1 gram n-undecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XIX

Four drops of one of the di-isoamylene mixtures produced according to Example I is added to 1 gram of n-dodecyl dimethyl amine oxide to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XX

One gram of n-tridecyl dimethyl amine oxide is admixed with eight drops of one of the di-isoamylene compositions of Example I. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "clean fresh, woody, herbaceous, piney" aroma; whereas without the use of one of the di-isoamylene compositions of Example I, the bleached laundry has a faint characteristic disagreeable "hypochlorite" aroma.

EXAMPLE XXIA

Aromox ® DMMC-W in various quantities is mixed with 0.1 gram of one of the di-isoamylene compositions prepared according to Example I. The resulting premixes are then added to 200 grams of an aqueous 5% sodium hypochlorite solution. Sufficient 12.5 M aqueous NaOH is added to bring the pH of the mixture up to 13. The following results are obtained:

| Percentage Aromox DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When used as laundry bleaches, the resulting bleached laundries on dry-out in an atmosphere of 50% relative humidity in each of the three cases above retain a "clean fresh", "woody", "herbaceous", "piney" aroma whereas without the use of one of the diisoamylene products prepared according to Example I, the bleached laundry has a faint characteristic disagreeable hypochlorite aroma.

EXAMPLE XXIB

Dowfax ® 2A1 (see Note 1, infra) in various quantities, as set forth below, is mixed with 0.1 gram of one of the diisoamylene compositions prepared according to Example I. The resulting premixed are then added to 200 grams of an aqueous 7% sodium hypochlorite solution. Sufficient 12.5 M aqueous NaOH is added to bring the pH of the mixture up to 13.5. The following results are obtained:

| Percentage of DOWFAX ® 2A1 | Clarity of hypochlorite solution after addition of premix |
|---|---|
| 0.23% | Clear after seven days |
| 0.15% | Clear after five days |
| 0.08% | Clear after three days |
| 0.01% | Initially slightly turbid; two phases exist after three days. |

FIG. 5A represents a graph of *percent residual chlorine* versus *time in hours* for hypochlorite solutions containing DOWFAX ® 2A1 (a registered trademark of the Dow Chemical Company of Midland, Mich.) identifying the compound having the structure:

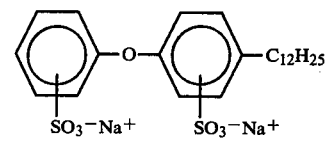

wherein the $C_{12}H_{25}$ moiety is branched chain and the $SO_3^-Na^+$ moieties are at various positions on each of the benzene rings. or AROMOX ® DMMC-W, a 30% aqueous solution of dimethylcocoamine oxide having the structure:

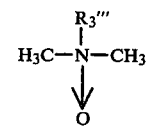

a trademark of Akzo Corporation of Chicago, Ill. (product produced by Armac, Division of Akzo Corporation of Chicago, Ill.) with the ratio of AROMOX ® DMMC-W:base being 0.8:99 and the ratio of DOWFAX ® 2A1:base being 0.8:99.

FIG. 5B is a graph of *percent residual chlorine* versus *time in hours* for hypochlorite solutions of (1) DOWFAX ® 2A1 and AROMOX ® DMMC-W in the absence of fragrance or essential oils with the ratios of AROMOX ® DMMC-W:base being 1.8:99 and 3.8:96 and the ratios of DOWFAX ® 2A1:base being 1.8:99 and 3.8:99.

FIG. 6A is a graph of *percent residual chlorine* versus *time in hours* comparing the performance of hypochlorite solutions containing (i) DOWFAX ® B 2A1 versus (ii) AROMOX® DMMC-W using a diisoamylene product produced according to Example I or not using any fragrance or essential oils with the ratio of AROMOX® DMMC-W:diisoamylene:base being 3.8:0.2:96 and the ratio of DOWFAX® 2A1:diisoamylene:base being 3.8:0.2:96

FIG. 6B is a graph of *percent residual chlorine* versus *time in hours* comparing hypochlorite solutions of DOWFAX® 2A1 versus AROMOX® DMMC-W with the perfuming material being one of the diisoamylene products produced according to Example I, wherein the ratio of AROMOX® DMMC-W:diisoamylene:base is either 0.8:0.2:99 or 1.8:0.2:98 and the ratio of DOWFAX® 2A1:diisoamylene:base is 0.8:0.2:99 or 1.8:0.2:98.

Note 1: Dowfax® 2A1 is a material consisting essentially of a mixture of compounds defined according to the structure:

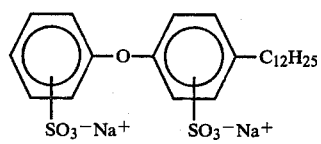

wherein the $C_{12}H_{25}$ moiety is branched chain and the $SO_3^-Na^+$ moieties are at various positions on each of the benzene rings.

EXAMPLE XXII

Dowfax® 3B2 (see Note 2, infra) in various quantities, as set forth below, is mixed with 0.1 gram of one of the diisoamylene compositions prepared according to Example I. The resulting premixes are then added to 200 grams of an aqueous 7% sodium hypochlorite solution. Sufficient 12.5 M aqueous NaOH is added to bring the pH of the mixture up to 13.5. The following results are obtained:

| Percentage of DOWFAX® 2A1 | Clarity of hypochlorite solution after addition of premix |
| --- | --- |
| 0.23% | Clear after seven days |
| 0.15% | Clear after five days |
| 0.08% | Clear after three days |
| 0.01% | Initially slightly turbid; two phases exist after three days. |

When used as laundry bleaches, the resulting bleached laundries on dry-out in an atmospher of 50% relative humidity in each of the four cases above retain a "woody", "herbaceous", "piney" aroma whereas without the use of the diisoamylene materials prepared according to Example I, the bleached laundry has a faint characteristic disagreeable hypochlorite aroma.

Note 2: Dowfax® 3B2 is a mixture of compounds essentially defined according to the structure:

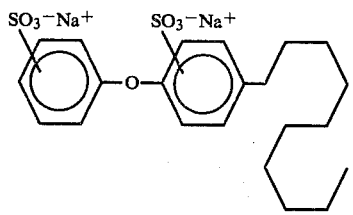

wherein the $SO_3^-Na^+$ moieties are at various positions on the phenyl moieties. Dowfax® 3B2 is a registered trademark of the Dow Chemical Company of Midland, Mich.

In the following examples, Aromox® DMC-W and Aromox® DMMC-W are 30% aqueous solutions of dimethyl cocoamine oxide; and Aromox® NCMDW is a 40% aqueous solution of N-cocomorpholine oxide produced by Armac Division of AKZO of Chicago, Ill.

EXAMPLE XXIII

Four drops of one of the di-isoamylene compositions prepared according to Example I is added to two grams of Dowfax® 3B2 and 0.5 grams of Aromox® DMC-W to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of seven days. When the 5% aqueous sodium hpochlorite solution is used as a laundry bleach, the resulting laundry on dry-out in an atmosphere of 65% relative humidity yields substantially no characteristic "hypochlorite" odor but does have a faint pleasant "woody/piney/herbaceous" aroma. Futhermore, no such characteristic "hypochlorite" aroma is retained on the hands of the individual handling such laundry in both the wet and the dry states.

EXAMPLE XXIV

One gram of Dowfax® 3B2; one gram of Dowfax® 2A1 and 0.25 grams of Aromox® DMMC-W is admixed with eight drops of one of the di-isoamylene compositions of Example I. This premix is then added, with stirring to 200 grams of a mixture containing 4.5% aqueous sodium hypochlorite and 4.5% aqueous lithium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh", woody, herbaceous, piney aroma; whereas without the use of one of the diisoamylene products prepared according to Example I, the bleached laundry has a faint characteristic disagreeable "hypochlorite" aroma.

EXAMPLE XXV

One gram of Dowfax® 2A1 and one gram of Dowfax® 3B2 is admixed with eight drops of one of the di-isoamylene compositions of Example I. This premix is then added, with stirring to 200 grams of a mixture containing 4.5% aqueous sodium hypochlorite. Sufficient 4 M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh", woody, herbaceous, piney aroma; whereas without the use of one of the diisoamylene products prepared according to Example I, the bleached laundry has a faint characteristic disagreeable "hypochlorite" aroma.

EXAMPLE XXVI 1.5 grams of Dowfax® 2A1 is admixed with eight drops of one of the di-isoamylene products produced according to Example I. This premix is then added with stirring to 200 grams of a mixture containing 4.5% aqueous sodium hypochlorite and 4.5% aqueous lithium hypochlorite. Sufficient 2 M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting bleached laundry, on dry-out in an atmosphere of 50% relative humidity, retains a "woody, herbaceous, piney" aroma whereas without the use of one of the diisoamylene compositions of Example I, the bleached laundry has a faint characteristic disagreeable "hypochlorite" aroma.

EXAMPLE XXVII

Four drops of one of the di-isoamylene mixtures produced according to Example I is added to 1.0 grams of Dowfax® 3B2 and 0.25 grams of Aromox® NCMDW to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XXVIII

Four drops of one of the di-isoamylene mixtures produced according to Example I, is added to 0.1 gram n-undecyl dimethyl amine oxide and 0.9 grams of Dowfax® 3B2 to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Futhermore, no such characteristic "hypochlorite" aroma is retained on the hands of the individual handling such laundry in both the wet and the dry states.

EXAMPLE XXIX

Four drops of one of the di-isoamylene mixtures produced according to Example I is added to 0.1 gram of n-docecyl dimethyl amine oxide and 0.9 grams of Dowfax® 2A1 to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XXX 0.2 grams of n-tridecyl dimethyl amine oxide and 0.7 grams of Dowfax® 3B2 are admixed with eight drops of one of the di-isoamylene compositions of Example I. This premix is then added with stirring to 200 grams of a 7% aqueous solution of lithium hypochlorite. Sufficient 3 M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a "clean fresh, woody, herbaceous, piney" aroma; whereas without the use of the di-isoamylene compositions of Example I, the bleached laundry has a faint characteristic disagreeable "hypochlorite" aroma.

EXAMPLE XXXI

A mixture is prepared consisting of 39 grams Dowfax® 2A1 (60.75%); 4.5 grams sodium palmitate (7.00%); and 20.7 grams of water (32.25%). The mixture is heated while stirring followed by ultrasonic dispersion thereby yielding a homogeneous gel. 64.2 grams of this material is used as follows: 4 drops of one of the diisoamylene mixtures produced according to Example I is added to 2.0 grams of the foregoing gel to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XXXII

A mixture is prepared consisting of 39 grams Dowfax® 2A1 (60.75%); 4.5 grams sodium laurate (7.00%); and 20.7 grams of water (32.25%). The mixture is heated while stirring followed by ultrasonic dispersion thereby yielding a homogeneous gel. 64.2 grams of this material is used as follows: 4 drops of one of the diisoamylene mixtures produced according to Example I is added to 2.0 grams of the foregoing gel to produce a clear premix. The clear premix is added to 200 grams of CLOROX® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XXXIII

A mixture is prepared consisting of 20.1 grams Dowfax ® 2A1 (60.75%); 2.0 grams sodium palmitate (7.00%); and 20.0 grams of water (32.25%). The mixture is heated while stirring followed by ultrasonic dispersion thereby yielding a homogeneous gel. 64.2 grams of this material is used as follows: 4 drops of one of the diisoamylene mixtures produced according to Example I is added to 2.0 grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XXXIV

A mixture is prepared consisting of 20.1 grams Dowfax ® 2A1 (60.75%); 2.0 grams sodium laurate (7.00%); and 20.0 grams of water (32.25%). The mixture is heated while stirring followed by ultrasonic dispersion thereby yielding a homogeneous gel. 64.2 grams of this material is used as follows: 4 drops of one of the diisoamylene mixtures produced according to Example I is added to 2.0 grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

EXAMPLE XXXV

A mixture is prepared consisting of 10 grams Dowfax ® 2A1 and 10 grams Dowfax ® 3B2 (60.75%); and 2.0 grams sodium laurate (7.00%); and 20.0 grams of water (32.25%). The mixture is heated while stirring followed by ultrasonic dispersion thereby yielding a homogeneous gel. 64.2 grams of this material is used as follows: 4 drops of one of the diisoamylene mixtures produced according to Example I is added to 2.0 grams of the foregoing gel to produce a clear premix. The clear premix is added to 200 grams of CLOROX ® with stirring resulting in a clear stable single phase solution. Sufficient 1 M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant "woody, herbaceous, piney" aroma. Furthermore, no such characteristic "hypochlorite" aroma is retained on the hands of the individual handling such laundry in both the wet and the dry states.

What is claimed is:

1. An aqueous alkali metal hypochlorite solution comprising as a sole detergent a composition of matter selected from the group consisting of (1) at least one substance defined according to the structure:

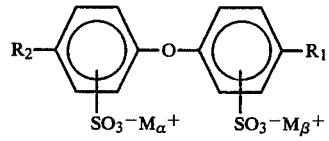

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl the other of $R_1$ or $R_2$ is hydrogen; wherein $M_\alpha$ and $M_\beta$ are the same or different and each represents alkali metal consisting of sodium, potassium and lithium and (2) a mixture comprising a material having the structure:

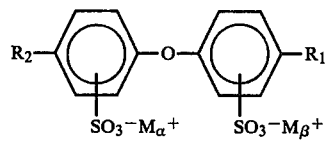

and intimately admixed therewith a substance having the structure:

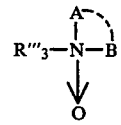

wherein $R_3'''$ is straight chain alkyl; wherein more than 55% of the $R_3'''$ moieties consist of straight chain alkyl having from 11 up to 13 carbon atoms and wherein A and B are each separately methyl or, taken together, complete a morpholine ring; and from 0.02% up to 0.2% of one or more diisoamylene-containing compositions produced by the step of reacting 2 moles of diisoamylene in the presence of an acid catalyst whereby a mixture of compounds is formed which mixture consists essentially of compounds defined according to the generic structure:

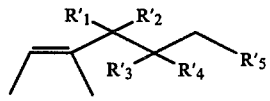

wherein $R'_1$, $R'_2$, $R'_3$, $R'_4$ and $R'_5$ are the same or different and each represents hydrogen or methyl with the provisos that (i) the sum total of the carbon atoms in $R'_1$, $R'_2$, $R'_3$, $R'_4$ and $R'_5$ is 3; and (ii) $R'_1$, and $R'_2$ represents hydrogen when $R'_5$ represents methyl; and (iii) when either $R'_1$ or $R'_2$ is methyl, $R'_5$ is hydrogen; said diisoamylene being capable of imparting to said alkali metal hypochlorite solution or to a article to which the said alkali metal hypochlorite solution is applied, a woody, piney, herbaceous aroma, said hypochlorite solution having a pH of 11 up to 14.0.

2. The composition of claim 1 wherein the compound having the structure:

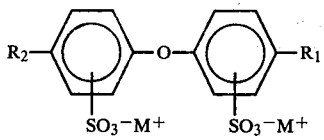

is selected from the group of materials having the structures:

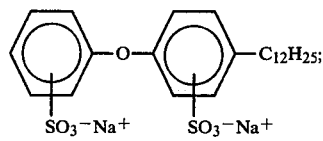

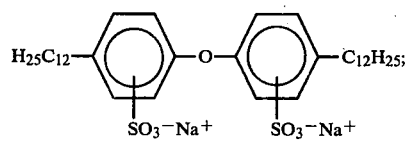

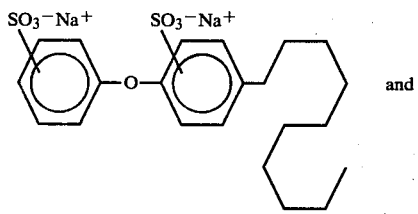

and

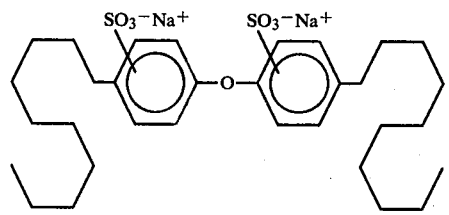

3. A process for producing a stable single phase aqueous alkaline metal hypochlorite solution having a woody, piney and herbaceous fragrance consisting, in sequential order, of the steps of (a) adjusting the pH of an aqueous alkali metal hypochlorite solution to the range of 11-14.0; (b) admixing a composition of matter selected from the group consisting of: (i) a chemical compound having the structure:

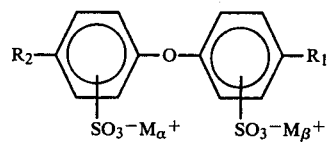

wherein at least one of $R_1$ and $R_2$ is $C_{10}$–$C_{12}$ straight chain or branched chain alkyl and $M_\alpha$ and $M_\beta$ are the same or different and each represents alkali metal selected from the group consisting of lithium, potassium and sodium and (ii) a mixture of at least one compound having the structure:

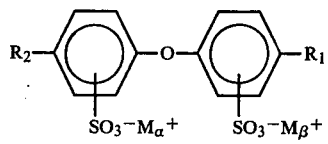

and a compound having the structure:

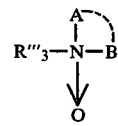

wherein $R_3'''$ is straight chain alkyl; wherein more than 55% of the $R_3'''$ moieties consist of straight chain alkyl having from 11 up to 13 carbon atoms and wherein A and B are each separately methyl or taken together complete a morpholine ring with a composition consisting essentially of a diisoamylene compound, produced by dimerizing 2-methyl-2-butene with an acid, whereby a premix is formed and (iii) adding said premix to the pH-adjusted hypochlorite solution.

4. The process of claim 3 comprising the additional step of adding to said premix a gel-forming agent selected from the group consisting or sodium palmitate, lithium palmitate, potassium palmitate, sodium laurate, lithium laurate, potassium laurate, sodium stearate, potassium stearate and lithium stearate.

5. The composition of claim 1 comprising in addition to the ingredients of said composition, a thickening or gel-forming agent selected from the group consisting of sodium laurate, potassium laurate, lithium laurate, sodium palmitate, potassium palmitate, lithium palmitate, sodium stearate, potassium stearate and lithium stearate.

* * * * *